(12) United States Patent
Ignatova et al.

(10) Patent No.: US 11,434,485 B2
(45) Date of Patent: Sep. 6, 2022

(54) SYNTHETIC TRANSFER RNA WITH EXTENDED ANTICODON LOOP

(71) Applicant: Arcturus Therapeutics, Inc., San Diego, CA (US)

(72) Inventors: Zoya Ignatova, Hamburg (DE); Andrew Torda, Hamburg (DE); Marco Matthies, Hamburg (DE)

(73) Assignee: ARCTURUS THERAPEUTICS, INC., San Diego, CA (US)

( * ) Notice: Subject to any disclaimer, the term of this patent is extended or adjusted under 35 U.S.C. 154(b) by 0 days.

(21) Appl. No.: 16/980,927

(22) PCT Filed: Mar. 14, 2019

(86) PCT No.: PCT/EP2019/056429
§ 371 (c)(1),
(2) Date: Sep. 15, 2020

(87) PCT Pub. No.: WO2019/175316
PCT Pub. Date: Sep. 19, 2019

(65) Prior Publication Data
US 2020/0407714 A1 Dec. 31, 2020

(30) Foreign Application Priority Data
Mar. 15, 2018 (DE) .................... 10 2018 106 080.7
Mar. 15, 2018 (LU) ...................................... 100734

(51) Int. Cl.
*C12N 15/11* (2006.01)
*A61K 48/00* (2006.01)

(52) U.S. Cl.
CPC .............. *C12N 15/11* (2013.01); *A61K 48/00* (2013.01); *C12N 2310/3513* (2013.01); *C12N 2310/531* (2013.01)

(58) Field of Classification Search
CPC ............ C12N 15/11; C12N 2310/3513; C12N 2310/531; A61K 48/00
See application file for complete search history.

(56) References Cited

U.S. PATENT DOCUMENTS 6,964,859 B2   11/2005  Rajbhandary et al.

OTHER PUBLICATIONS

Anderson et al , Exploring the Limits of Codon and Anticodon Size, Chemistry and Biology, 2002, vol. 9: 237-244 (Year: 2002).*
Atkinson et al, Mutations to nonsense codons in human genetic disease: implications for gene therapy by nonsense suppressor tRNAs, Nucleic Acid Research, 1994, vol. 22, No. 8: 1327-1334 (Year: 1994).*
Bozon et al, Identification of Four New Mutations in the Cystic Fibrosis Transmembrane Conductance Regulator Gene: IMT, L1077P, Y1092X, 2183Alk+G, Human Mutation, 1994, 3: 330-332 (Year: 1994).*
GenBank NM_000492.4 , CFTR mRNA and protein sequence, 1992, pp. 1-11 (Year: 1992).*
Breitschopf et al, Identity elements of human tRNALeu: structural requirements for converting human tRNASer into a leucine acceptor in vitro, Nucleic Acids Research, 1995, vol. 23, No. 18, pp. 3633-3637 (Year: 1995).*
Maini et al , Ribosome-Mediated Incorporation of Dipeptides and Dipeptide Analogues into Proteins in Vitro, JACS, 2015, 137: 11206-11209 (Year: 2015).*
Ohashi et al, Primary Sequence of Glutamic Acid tRNA II From *Escherichia Coli*, FEBS Letters, 1972, vol. 20, 2: 239-241 (Year: 1972).*
Kirill A. Afonin: "In Silico Design and Enzymatic Synthesis of Functional RNA Nanoparticles", ACS Publications, Accounts of Chemical Research, 2014, vol. 47, pp. 1731-1740.
Pascal Auffinger, et al: "An extended structural signature for the tRNA anticodon loop", RNA (2001), 7:344-341, Cambridge University Press, Printed in the USA.
Renata Bordeira-Carrico, et al: "Rescue of wild-type E-cadherin expression from nonsense-mutated cancer cells by a suppressor-tRNA", www.nature.com/ejhg, European Journal of Human Genetics (2014) vol. 22, pp. 1085-1092; doi: 10.1038/ejhg.2013.292; published online Jan. 15, 2014.
John C. Burnett, et al: "RNA-based Therapeutics-Current Progress and Future Prospects", Chem. Biol. Jan. 27, 2012; 19(1): pp. 60-71, doi: 10.1016/j.chembiol.2011.12.008.
Michael R. Culbertson, et al: "Frameshift Suppression in *Saccharomyces cerevisiae*. V. Isolation and Genetic Properties of Nongroup-Specific Suppressors", Genetics 102: pp. 361-378, Nov. 1982.
Andreas Czech, et al: "Reversible and Rapid Transfer-RNA Deactivation as a Mechanism of Translational Repression in Stress", www.plosgenetics.org, PLOS Genetics, Aug. 2013, vol. 9, Issue 8, pp. 1-9.
A. I. Esterhuizen, et al: "Duchenne muscular dystrophy; High-resolution melting curve analysis as an affordable diagnostic mutation scanning tool in South African cohort", SAMJ, Nov. 2014, vol. 104, No. 11, pp. 779-784.
Kohei Fujikura: "Premature termination codons in modern human genomes", www.nature.com/scientificreports, Scientific Reports, 6:22468, pp. 1-9, DOI: 10.1038/srep22468.
Roberto Gambari, et al: "Therapy for Cystic Fibrosis Caused by Nonsense Mutations", http://dx.doi.org/10.5772/61053, Chapter 13, pp. 309-326.

(Continued)

*Primary Examiner* — Ekaterina Poliakova-Georgantas
(74) *Attorney, Agent, or Firm* — Mintz, Levin, Cohn, Ferris, Glovsky and Popeo, P.C.

(57) ABSTRACT

A synthetic transfer RNA with an extended anticodon loop. A synthetic suppressor transfer RNA useful for the treatment of a genetic disease like cystic fibrosis associated with a nonsense mutation. The synthetic transfer RNA contains an extended anticodon loop with two consecutive anticodon base triplets configured to base-pair to two consecutive codon base triplets on an mRNA. The first anticodon base triplet or the second anticodon base triplet is configured to base-pair to a stop codon base triplet on the mRNA.

3 Claims, 8 Drawing Sheets

Figure 1:
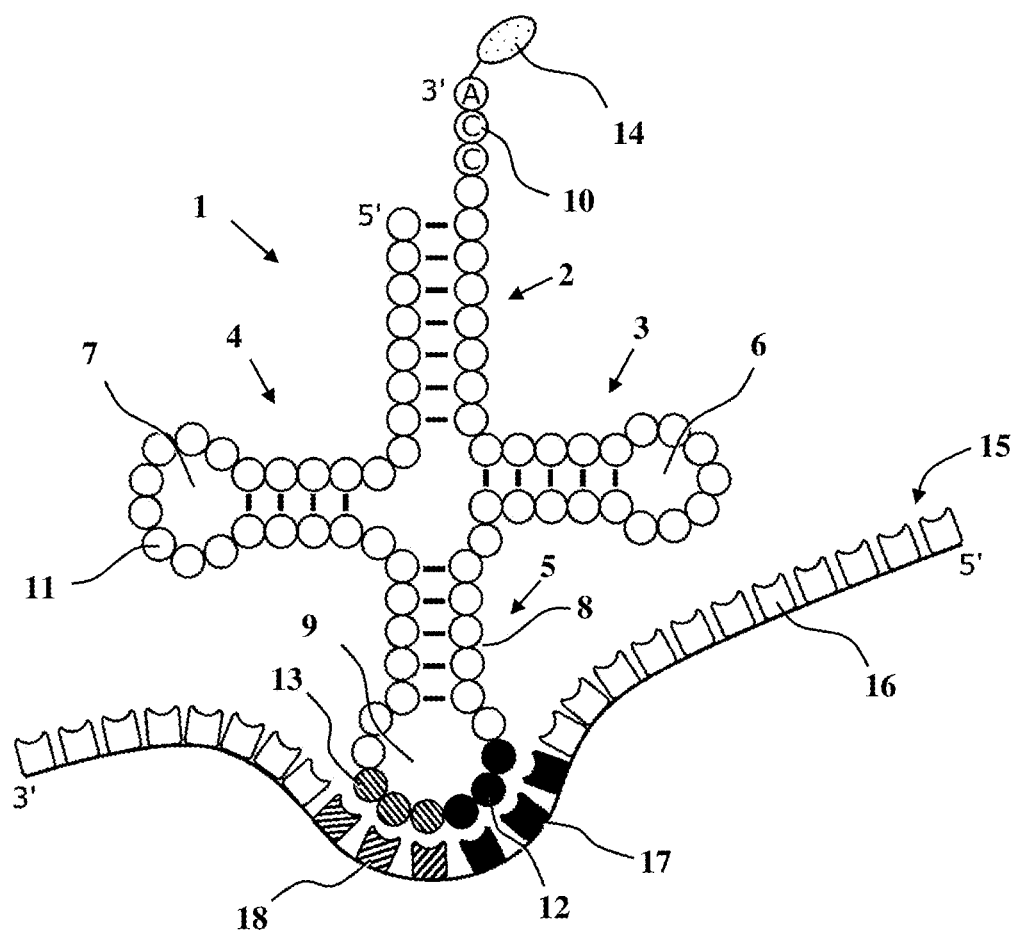

Specification includes a Sequence Listing.

(56) References Cited

OTHER PUBLICATIONS

Renaud Geslain, et al: "Functional analysis of human tRNA isodecoders", J. Mol. Biol.. Feb. 26, 2010; 396(3): 821.doi:10.1016/j.jmb.2009.12.018.

Takahiro Hohsaka, et al: "Incorporation of non-natural amino acids into proteins", Chemical Biology 2002, 6:809-815, published online Oct. 18, 2002.

Kim M. Keeling, et al: "Gentamicin-mediated suppression of Hurler syndrome stop mutations restores a low level of α-L-iduronidase activity and reduces lysosomal glycosaminoglycan accumulation", Human Molecular Genetics, 2001, vol. 10, No. 3, pp. 291-299.

Ramesh Koukuntla: "Suppressor tRNA mediated gene therapy" (2009), Iowa State University, Graduate Theses and Dissertations, http://lib.dr.iastate.edu/etd/10920, pp. 1-116.

John D. Lueck, et al: "Engineered tRNA suppression of a CFTR nonsense mutation", bioRxiv preprint first posted online Nov. 20, 2016; doi: http://dx.doi.org/10.1101/088690, pp. 1-9.

Thierry Meinnel, et al: "Maturation of Pre-tRNAfMet by *Escherichia coli* RNase P Is Specified by a Guanosine of the 5'-Flanking Sequence", The Journal of Biological Chemistry, vol. 270, No. 26, Issue of Jun. 30, pp. 15908-15914, 1995, printed in USA.

Emilie Vallieres, et al: "Cystic fibrosis gene mutations: evaluation and assessment of disease severity", Advances in Genomics and Genetics, 2014:4, pp. 161-172.

Michael Wilschanski: "Class 1 CF mutations", www.frontiersin.org, Frontiers in Pharmacology, Opinion Article, published : Jun. 20, 2012, vol. 3, Article 117, pp. 1-3, doi: 10.3389/fphar.2012.00117.

International Preliminary Report on Patentability dated Sep. 15, 2020, in International Application No. PCT/EP2019/056429.

Hohsaka et al. (Sep. 1, 2001) "Five-base codons for incorporation of Nonnatural Amino Acids into Proteins", Nucleic Acids Research, 29(17):3646-3651.

Hohsaka (Jun. 1, 2004) "Incorporation of Nonnatural Amino Acids into Proteins through Extension of the Genetic Code", Bulletin of the Chemical Society of Japan, 77(6):1041-1049.

Hohsaka et al. (Jan. 1, 2000) "Incorporation of Nonnatural Amino Acids into Proteins by Using Five-Base Codon-Anticodon Pairs", Nucleic Acids Symposium Series, 44:99-100.

Hendrickson et al. (Mar. 26, 2004) "Incorporation of Nonnatural Amino Acids into Proteins", Annual Review of Biochemistry, 73:147-176.

* cited by examiner

SYNTHETIC TRANSFER RNA WITH EXTENDED ANTICODON LOOP

REFERENCE TO A SEQUENCE LISTING

The instant application contains a Sequence Listing which has been submitted electronically in ASCII format and is hereby incorporated by reference in its entirety. Said ASCII copy, created on Sep. 15, 2020 is named 3960053_SEQUENCE_LISTING.txt and is 22.32 kilobytes in size.

The invention relates to a synthetic transfer RNA with an extended anticodon loop.

Transfer ribonucleic acids (tRNAs) are an essential part of the protein synthesizing machinery of living cells and are necessary components for translating the nucleotide sequence of a messenger RNA (mRNA) into the amino acid sequence of a protein. Naturally occurring tRNAs comprise an amino acid-binding stem being able to covalently bind an amino acid and an anticodon loop containing a base triplet called "anticodon", which can bind non-covalently to a corresponding base triplet called "codon" on an mRNA. A protein is synthesized by assembling the amino acids carried by tRNAs using the codon sequence on the mRNA as a template with the aid of a multi component system comprising, i.a., the ribosome and several auxiliary enzymes.

Some diseases belonging to the group of genetic disorders are based on a change in genetic information, e.g. a mutation in the DNA of the encoding genes. In this case the mRNA transcribed from the mutated gene will also carry the altered genetic information and an aberrant, possibly non-functional protein is formed. A mutation may, for example, lead to the introduction of a stop codon within a coding region, resulting in premature termination of protein synthesis and the production of a truncated protein. As an example, disease cystic fibrosis (CF) can be caused by a mutation of the gene coding for the membrane protein "cystic fibrosis transmembrane conductance regulator" (CFTR). In this case, the mutation introduces a premature termination codon (PTC) or stop codon within the reading frame of the CFTR gene (Vallières E, Elborn J S, Cystic fibrosis gene mutations: evaluation and assessment of disease severity. Advances in Genomics and Genetics, Volume 2014:4 Pages 161-172; Wilschanski M. Class 1 CF Mutations. Frontiers in Pharmacology. 2012; 3:117. doi:10.3389/fphar.2012.00117; Gambari R, Breveglieri G, Salvatori F, Finotti A, Borgatti M, 2015, Therapy for Cystic Fibrosis Caused by Nonsense Mutations, Cystic Fibrosis in the Light of New Research, Wat D. (Ed.), InTech, DOI: 10.5772/61053).

Stop codon suppressor agents like aminoglycosides promoting translational readthrough for recovering a functional CFTR in CF with PTCs have been described in the scientific literature (see, e.g., Mutyam V, Du M, Xue X, Keeling K M, White E L, Bostwick J R, Rasmussen L, Liu B, Mazur M, Hong J S, Falk Libby E, Liang F, Shang H, Mense M, Suto M J, Bedwell D M, Rowe S M. Discovery of Clinically Approved Agents That Promote Suppression of Cystic Fibrosis Transmembrane Conductance Regulator Nonsense Mutations. Am J Respir Crit Care Med. 2016 Nov. 1; 194(9):1092-1103. doi 10.1164/rccm.201601-0154OC; Gambari R, Breveglieri G, Salvatori F, Finotti A, Borgatti M, 2015, Therapy for Cystic Fibrosis Caused by Nonsense Mutations, Cystic Fibrosis in the Light of New Research, Wat D. (Ed.), InTech, DOI: 10.5772/61053). Such agents, however, are often neither effective nor well tolerated.

Although still in its beginnings, gene therapy involving the introduction of corrective genetic material into the cells of a patient, is becoming more and more important for treating genetic diseases. Currently, gene therapy approaches are primarily based on the use of mRNA in order to replace and compensate for a mutated "defective" mRNA. However, mRNA is short-lived and the length of the mRNA sequences presents problems for therapeutic application. A particular mRNA may, for example, be longer than the cargo capacity of currently available vectors for gene delivery and therapy.

Compared to mRNA, tRNA molecules offer significantly higher stability and are on average 10-fold shorter, alleviating the problem of introduction into the target tissue. This has led to attempts to use tRNA in gene therapy in order to prevent the formation of a truncated protein from an mRNA with a premature stop codon and to introduce the correct amino acid instead (see, e.g., Koukuntla, R 2009, Suppressor tRNA mediated gene therapy, Graduate Theses and Dissertations, 10920, Iowa State University, http://lib.dr.iastate.edu/etd/10920; US 2003/0224479 A1; U.S. Pat. No. 6,964,859).

Lueck et al. (Lueck, J. D., Infield, D T, Mackey, A L, Pope, R M, McCray, P B, Ahern, C A. Engineered tRNA suppression of a CFTR nonsense mutation, bioRxiv 088690; doi: 10.1101/088690), for example, describe a codon-edited tRNA enabling the conversion of an in-frame stop codon in the CFTR gene to the naturally occurring amino acid in order to restore the full-length wild type protein.

Sako et al. (Sako Y, Usuki F, Suga H. A novel therapeutic approach for genetic diseases by introduction of suppressor tRNA. Nucleic Acids Symp Ser (Oxf). 2006; (50):239-40. PubMed PMID: 17150906, doi: 10.1093/nass/nrl119) describe an approach to read through PTC-containing mRNAs using suppressor tRNA that is introduced to cells by transfection. Nonsense triplet codons were suppressed and four-base codons were read by the corresponding suppressor tRNAs derived from human tRNA (Ser).

tRNAs with an extended anticodon loop comprising a four-base or five-base anticodon have also been described for incorporating unnatural amino acids into proteins (US 2006/0177900 A1; WO 2005/007870; Hohsaka T, Ashizuka Y, Murakami H, Sisido M. Five-base codons for incorporation of nonnatural amino acids into proteins. Nucleic Acids Research. 2001; 29(17):3646-3651; Hohsaka T, Sisido M. Incorporation of non-natural amino acids into proteins. Curr Opin Chem Biol. 2002 December; 6(6):809-15. Review. PubMed PMID: 12470735). Anderson et al. (Anderson J C, Magliery T J, Schultz P G. Exploring the limits of codon and anticodon size. Chem Biol. 2002 February; 9(2):237-44. DOI: 10.1016/S1074-5521(02)00094-7) describe the suppression of two-, three-, four-, five-, and six-base codons with tRNAs containing 6-10 nt in their anticodon loops.

There is still a need for counteracting the effects of and/or suppressing a nonsense mutation. It is therefore an object of the invention to provide such means, in a particular a nonsense mutation suppressor for the treatment of a genetic disease like cystic fibrosis associated with a nonsense mutation.

In one aspect the invention provides a synthetic transfer ribonucleic acid (tRNA), the synthetic transfer RNA comprising an extended anticodon loop with two consecutive anticodon base triplets configured to base-pair to two consecutive codon base triplets on an mRNA, wherein the first anticodon base triplet or the second anticodon base triplet is configured to base-pair to a stop codon base triplet on the mRNA.

The invention provides novel suppressor tRNAs that can be used to suppress a nonsense mutation, e.g. for restoring the ability of a cell to synthesize a functional protein from an mRNA having a mutation in its coding sequence, which would otherwise lead to premature cessation of translation and a truncated protein. The synthetic tRNA of the invention comprises an extended anticodon loop having two consecutive anticodon base triplets, at least one of which being able to base-pair to a stop codon base triplet on an mRNA. The synthetic tRNA of the invention is thus able to bind to two adjacent codons on the mRNA, one being a premature termination codon (PTC), which are complementary to the two anticodon base triplets. The synthetic tRNA of the invention not only base-pairs with the PTC but also with the preceding or following codon on the mRNA resulting in the incorporation of an amino acid carried by the tRNA into the growing amino acid chain instead of a premature termination of the protein synthesis. Unless the synthetic tRNA of the invention is (pre)aminoacylated with a dipeptide, the resulting protein will have one amino acid less than the wild-type protein, i.e. a protein synthesized from the wild-type mRNA without the PTC, but the chances are good that this will nevertheless lead to a functional protein. Advantageously, the base-pairing of the synthetic tRNA of the invention with two adjacent codons, one of which being a PTC and the other being a specific codon adjacent to the PTC, on the mRNA is associated with higher specificity compared to suppressor tRNAs binding only to a single codon, i.e. a stop codon. Consequently, the synthetic tRNA of the invention can be designed to only bind to a specific combination of a PTC and one of its neighbouring codons, considerably reducing the risk of unwanted pairing to PTCs or "normal" stop codons on non-targeted mRNA.

The terms "transfer ribonucleic acid" or "tRNA" refer to RNA molecules with a length of typically 73 to 90 nucleotides, which mediate the translation of a nucleotide sequence in messenger RNA into the amino acid sequence of a protein. tRNAs are able to covalently bind a specific amino acid at their 3' CCA tail at the end of the acceptor stem, and to base-pair via a three-nucleotide anticodon in the anticodon loop of the anticodon arm with a three-nucleotide sequence (codon) in the messenger RNA. Some anticodons can pair with more than one codon due to a phenomenon known as wobble base pairing. The secondary "cloverleaf" structure of tRNA comprises the acceptor stem binding the amino acid and three arms ("D arm", "T arm" and "anticodon arm") ending in loops (D loop, TψC loop, anticodon loop), i.e. sections with unpaired nucleotides. Aminoacyl tRNA synthetases charge (aminoacylate) tRNAs with a specific amino acid. Each tRNA contains a distinct anticodon triplet sequence that can base-pair to one or more codons for an amino acid. By convention, the nucleotides of tRNAs are often numbered 1 to 76, starting from the 5'-P terminus, based on a "consensus" tRNA molecule consisting of 76 nucleotides, and regardless of the actual number of nucleotides in the tRNA, which may deviate from 76 due to variable portions, e.g. the D loop, in the tRNA (see FIG. 3). Following this convention (also "tRNA numbering convention" in the following), nucleotide positions 34-36 of naturally occurring tRNA refer to the three nucleotides of the anticodon, and positions 74-76 refer to the terminating CCA tail. Any "supernumerary" nucleotide can, e.g., be numbered by adding alphabetic characters to the number of the previous nucleotide being part of the consensus tRNA and numbered according to the convention, for example 20a, 20b etc, or by independently numbering the nucleotides and adding a leading letter, as in case of the variable loop such as e11, e12 etc. (see, for example, Sprinzl M, Horn C, Brown M, Ioudovitch A, Steinberg S. Compilation of tRNA sequences and sequences of tRNA genes. Nucleic Acids Res. 1998; 26(1):148-53).

The terms "synthetic transfer ribonucleic acid" or "synthetic tRNA" refer to a non-naturally occurring tRNA. The term also encompasses analogues to naturally occurring tRNAs, i.e. tRNAs being structurally similar to naturally occurring tRNAs, but being modified in the base component, the sugar component and/or the phosphate component of one or more of the nucleotides, of which the tRNA is composed. The modified tRNA may, for example, have the phosphodiester backbone modified in that the phosphodiester bridge is replaced by a phosphorothioate, phosphoramidate or methyl phosphonate bridge. The sugar component may, for example, be modified at the 2' OH group, e.g. by dehydroxylating it to a deoxy ribonucleotide, or by replacing it with a methoxy-, methoxyethoxy- or aminoethoxy group. A synthetic transfer ribonucleic acid can, for example, be synthesized chemically and/or enzymatically in vitro, or in a cell based system, e.g. in a bacterial cell in vivo.

The term "codon" refers to a sequence of nucleotide triplets, i.e. three DNA or RNA nucleotides, corresponding to a specific amino acid or stop signal during protein synthesis. A list of codons (on mRNA level) and the encoded amino acids are given in the following:

| Amino acid | One Letter Code | Codons |
| --- | --- | --- |
| Ala | A | GCU, GCC, GCA, GCG |
| Arg | R | CGU, CGC, CGA, CGG, AGA, AGG |
| Asn | N | AAU, AAC |
| Asp | D | GAU, GAC |
| Cys | C | UGU, UGC |
| Gln | Q | CAA, CAG |
| Glu | E | GAA, GAG |
| Gly | G | GGU, GGC, GGA, GGG |
| His | H | CAU, CAC |
| Ile | I | AUU, AUC, AUA |
| Leu | L | UUA, UUG, CUU, CUC, CUA, CUG |
| Lys | K | AAA, AAG |
| Met | M | AUG |
| Phe | F | UUU, UUC |
| Pro | P | CCU, CCC, CCA, CCG |
| Ser | S | UCU, UCC, UCA, UCG, AGU, AGC |
| Thr | T | ACU, ACC, ACA, ACG |
| Trp | W | UGG |
| Tyr | Y | UAU, UAC |
| Val | V | GUU, GUC, GUA, GUG |

START: AUG
STOP: UAA, UGA, UAG, abbreviated "X"

The term "sense codon" as used herein refers to a codon coding for an amino acid. The term "stop codon" or "nonsense codon" refers to a codon, i.e. a nucleotide triplet, of the genetic code not coding for one of the 20 amino acids normally found in proteins and signalling the termination of translation of a messenger RNA. Stop codons (on the mRNA level) are UAA ("ochre"), UAG ("amber"), or UGA ("opal"). When describing the sequence of a protein, "X" (in one-letter code) or "Ter" (in three-letter code) is used to denote a stop codon. A nonsense mutation in a protein is often denoted with the wild-type amino acid, followed by the position of the amino acid in the protein, and an "X". As an example, "R553X" denotes a mutation of the codon coding for arginine (one-letter code R) to a stop codon (X) at position 553 in the protein (CFTR). A stop codon in an mRNA within an open reading frame leads to the production of a truncated, mostly non-active protein fragment.

The term "anticodon" refers to a sequence of three nucleotides that are complementary, that is bind or base-pair, to the three bases of the codon on the mRNA. If used herein, the terms "corresponding anticodon" or "corresponding codon" relate to an anticodon or a codon, which base-pairs with the respective complementary codon or anticodon. An anticodon may also contain nucleotides with modified bases.

The term "anticodon loop" refers to the unpaired nucleotides of the anticodon arm containing the anticodon. In naturally occurring tRNAs the anticodon loop is usually comprised of seven nucleotides, three of which pair to the codon in the mRNA.

The term "extended anticodon loop" refers to an anticodon loop with a higher number of nucleotides in the loop than in naturally occurring tRNAs. An extended anticodon loop may, for example, contain more than seven nucleotides, e.g. eight, nine, ten or eleven nucleotides.

The terms "codon base triplet" or "anticodon base triplet" refer to sequences of three consecutive nucleotides representing a codon or anticodon. The terms are used in order to clarify that the terms "codon" or "anticodon" as used herein in relation to the invention refer to nucleotide triplets, and not to sequences of four or more nucleotides, e.g. nucleotide quadruplets ("four base codons") etc. The two consecutive anticodon base triplets in the anticodon loop of a synthetic tRNA of the invention may, however, also be called "anticodon pair", "anticodon double", "anticodon duplex", "2×3 nt anticodon" or "anticodon tandem", and, correspondingly, the two consecutive codon base triplets in the mRNA "codon pair", "codon double", "codon duplex", "2×3 nt codon" or "codon tandem".

The term "base pair" refers to a pair of bases joined by hydrogen bonds. One of the bases of the base pair is usually a purine, and the other base is usually a pyrimidine. In RNA the bases adenine and uracil can form a base pair and the bases guanine and cytosine can form a base pair. However, the formation of other base pairs ("wobble base pairs") is also possible, e.g. base pairs of guanine-uracil (G-U), hypoxanthine-uracil (I-U), hypoxanthine-adenine (I-A), and hypoxanthine-cytosine (I-C). The term "being able to base-pair" refers to the ability of nucleotides or sequences of nucleotides to form hydrogen-bond-stabilized structures with a complementary nucleotide or nucleotide sequence.

The term "PTC" refers to a premature termination codon, i.e. a stop codon introduced into a coding nucleic acid sequence by a nonsense mutation, i.e. a mutation in which a sense codon, coding for one of the twenty proteinogenic amino acids specified by the standard genetic code, is changed to a chain-terminating codon. The term thus refers to a premature stop signal in the translation of the genetic code contained in mRNA. PTCs are implicated in a variety of genetic disorders, e.g. cystic fibrosis (DF), Duchenne muscular dystrophy (DMD), neurofibromatosis type 1 (NF1) or Hurler syndrome (MPS I). The term "premature stop codon" ("PSC") may be used synonymously for a premature termination codon, PTC.

The term "cystic fibrosis" refers to a genetic disorder inherited in an autosomal recessive manner. It is caused by mutations in both copies of the gene for the cystic fibrosis transmembrane conductance regulator (CFTR) protein. The term "nonsense mutation cystic fibrosis" (nmCF) may be used for CF caused by a nonsense mutation. Examples for nonsense mutation in the CFTR are W1282X (X=stop codon), G542X, R553X or R1162X.

The term "Duchenne muscular dystrophy" (DMD) (also "Becker muscular dystrophy", BMD) refers to a X-linked recessive genetic disorder characterized by progressive muscle degeneration and weakness caused by an absence of a functional dystrophin protein. The absence of dystrophin can be caused by a nonsense mutation in the dystrophin gene.

The term "neurofibromatosis type 1" (NF1 or NF-1), also called "Recklinghausen disease", is an autosomal dominant inherited disorder caused by the mutation of the NF1 gene on chromosome 17 coding for neurofibromin. NF1 causes tumours along the nervous system.

The term "Hurler syndrome" (also mucopolysaccharidosis type I, MPS I), relates to a genetic disorder causing accumulation of mucopolysaccharides (glycosaminoglycans, GAGs) due to a deficiency in alpha-L iduronidase. The most common PTC mutations in Hurler syndrome are W402X and Q70X (Scott H S, Litjens T, Hopwood J J, Morris C P, 1992, A common mutation for mucopolysaccharidosis type I associated with a severe Hurler syndrome phenotype, Hum Mutat.1: 103-108, doi 10.1002/humu.1380010204; Keeling K M, Brooks D A, Hopwood J J, Li P, Thompson J N, Bedwell D M, 2001, Gentamicin-mediated suppression of Hurler syndrome stop mutations restores a low level of α-1-iduronidase activity and reduces lysosomal glycosaminoglycan accumulation, Human Molecular Genetics 10, 291-300, doi 10.1093/hmg/10.3.291).

The terms "nonsense suppression" or "nonsense mutation suppression" refer to mechanisms masking the effects of a nonsense mutation and at least partly restoring the wild-type phenotype.

The term "suppressor tRNA" relates to a tRNA altering the reading of a messenger RNA in a given translation system. An example for a suppressor tRNA is a tRNA carrying an amino acid and being able to base-pair to a stop codon, so that the translation system can read through the stop codon. tRNAs that can recognize a stop codon are known as nonsense suppressor tRNAs or NSTs.

The term "homology" in relation to a nucleic acid refers to the degree of similarity or identity between the nucleotide sequence of the nucleic acid and the nucleotide sequence of another nucleic acid. Homology is determined by comparing a position in the first sequence with a corresponding position in the second sequence in order to determine whether identical nucleotides are present at that position. It may be necessary to take sequence gaps into account in order to produce the best possible alignment. For determining the degree of similarity or identity between two nucleic acids it is preferable to take a minimum length of the nucleic acids to be compared into account, for example at least 25%, 30%, 40%, 50%, 60%, 70%, 80%, 90%, 91%, 92%, 93%, 94%, 95%, 96%, 97%, 98%, 99%, 99.2% or 99.5% of the nucleotides in the respective sequences. Preferably the full length of the respective nucleic acid(s) is used for comparison. The degree of similarity or identity of two sequences can be determined by using a computer program such as muscle (Edgar, R. C. (2004), Muscle: multiple sequence alignment with high accuracy and high throughput, Nucleic Acids Research, 32, 1792-1797, doi: 10.1093/nar/gkh340) or mafft (Katoh, K. and Standley, D. M. (2013) MAFFT Multiple Sequence Alignment Software Version 7, Molecular Biology and Evolution, 30, 772-780, doi.org/10.1093/molbev/mst010). Where such terms like "x % homologous to" or "homology of x %" are used it means that two nucleic acid sequences have a sequence identity or similarity of x %, e.g. 50%.

The term "aminoacylation" relates to the enzymatic reaction charging a tRNA with an amino acid. An aminoacyl tRNA synthetase (aaRS) catalyses the esterification of a specific cognate amino acid or its precursor to a compatible cognate tRNA to form an aminoacyl-tRNA. The term "aminoacyl-tRNA" thus relates to a tRNA with an amino acid attached to it. Each aminoacyl-tRNA synthetase is highly specific for a given amino acid, and, although more than one tRNA may be present for the same amino acid, there is only one aminoacyl tRNA synthetase for each of the 20 proteinogenic amino acids. The terms "charge" or "load" may also be used synonymously for "aminoacylate". The term "aminoacylated" in relation to the synthetic tRNA of the invention relates to a synthetic tRNA already charged (precharged) with an amino acid or a dipeptide, such that the tRNA is already acylated when entering the target cell. The term "preaminoacylated" may synonymously be used in this context.

The term "modified nucleotides" (or "unusual nucleotides") in reference to tRNA relates to nucleotides having modified or unusual nucleotide bases, i.e. other than the usual bases adenine (A), uracil (U), guanine (G) and cytosine (C). Examples of modified nucleotides include 4-acetylcytidine (ac4c), 5-(carboxyhydroxymethyl)uridine (chm5u), 2'-O-methylcytidine (cm), 5-carboxymethylaminomethyl-2-thiouridine (cmnm5s2u), 5-carboxymethylaminomethyluridine (cmnm5u), dihydrouridine (d), 2'-O-methylpseudouridine (fm), beta, D-galactosylqueuosine (gal q), 2'-O-methylguanosine (gm), inosine (i), N6-isopentenyladenosine (i6a), 1-methyladenosine (m1a), 1-methylpseudouridine (m1f), 1-methylguanosine (m1g), 1-methylinosine (m1i), 2,2-dimethylguanosine (m22g), 2'-O-methyladenosine (am), 2-methyladenosine (m2a), 2-methylguanosine (m2g), 3-methylcytidine (m3c), 5-methylcytidine (m5c), N6-methyladenosine (m6a), 7-methylguanosine (m7g), 5-methylaminomethyluridine (mam5u), 5-methoxyaminomethyl-2-thiouridine (mam5s2u), beta, D-mannosylqueuosine (man q), 5-methoxycarbonylmethyl-2-thiouridine (mcm5s2u), 5-methoxycarbonylmethyluridine (mcm5u), 5-carbamoylmethyluridine (ncm5U), 5-carbamoylmethyl-2'-O-methyluridine (ncm5Um), 5-methoxyuridine (mo5u), 2-methylthio-N6-isopentenyladenosine (ms2i6a), N-((9-beta-D-ribofuranosyl-2-methylthiopurine-6-yl)carbamoyl) threonine (ms2t6a), N-((9-beta-D-ribofuranosylpurine-6-yl) N-methylcarbamoyl)threonine (mt6a), uridine-5-oxyacetic acid-methylester (mv), uridine-5-oxyacetic acid (o5u), wybutoxosine (osyw), pseudouridine (p, ψ) queuosine (q), 2-thiocytidine (s2c), 5-methyl-2-thiouridine (s2t), 2-thiouridine (s2u), 4-thiouridine (s4u), 5-methyluridine (t), N-((9-beta-D-ribofuranosylpurine-6-yl)-carbamoyl)threonine (t6a), 2'-O-methyl-5-methyluridine (tm), 2'-O-methyluridine (um), wybutosine (yw), 3-(3-amino-3-carboxy-propyl) uridine, (acp3)u (x).

The term "corresponding modified nucleotide" relates to a modified nucleotide at a given position in a sequence, which base has been modified based on the usual, i.e. unmodified, base of the nucleotide at the same position in the original sequence to be compared with the sequence containing the modified nucleotide. A corresponding modified nucleotide is thus any nucleotide that, in a cell, is usually produced from a usual nucleotide by modifying the usual nucleotide. A modified nucleotide corresponding to uridine, for example, is thus any nucleotide derived by the modification of uridine. As an example, 5-(carboxyhydroxymethyl)uridine (chm5u) at a particular position in a sequence may be a modified nucleotide corresponding to uridine at the same position in the original sequence. Further modified nucleotides corresponding to uridine are, for example, 5-methyluridine (t), 2'-O-methyl-5-methyluridine (tm), 2'-O-methyluridine (um), or 5-methoxyuridine (mo5u). Inosine, as another example, is produced from adenosine and thus is a modified nucleotide corresponding to adenosine.

The synthetic transfer RNA of the invention may be synthesized based on a naturally occurring tRNA. However, the tRNA of the invention is preferably designed computationally ("in silico") and synthesized chemically and/or enzymatically. The computational design of a synthetic tRNA according to the invention allows the design and synthesis of a tRNA that does not interfere with other tRNAs present in the cell. The synthetic tRNA of the invention is selected or designed in such a manner that an aminoacyl tRNA synthetase that naturally occurs in a living cell, preferably a mammalian cell, e.g. a human cell, is able to charge the tRNA with a specific amino acid. Preferably, the tRNA is selected or designed in such a manner that, under conditions within the cell, an amino acid is enzymatically attached to the tRNA that is encoded by the codon in a targeted mRNA next to a premature stop codon or by the wild-type codon mutated to the premature stop codon.

The skilled person is aware of the fact that a tRNA is aminoacylated with a specific amino acid by a specific aminoacyl tRNA synthetase (aaRS), and that the aaRS is able to recognize its cognate tRNA through unique identity elements at the acceptor stem and/or anticodon loop of the tRNA. In order to provide a tRNA which is loaded with its cognate amino acid in vivo, the skilled person will design the synthetic tRNA of the invention with suitable unique identity elements.

The tRNA of the invention preferably has a low sequence identity to any naturally occurring tRNA, and has preferably a sequence identity of less than 50%, especially preferred of less than 49%, 48%, 47%, 46%, 45%, 44% or 43%.

In the synthetic transfer RNA according to the invention the anticodon loop has been extended by a large enough number of nucleotides to accommodate the anticodon pair and to allow base-pairing with an mRNA. The anticodon loop of a synthetic transfer RNA of the invention may, for example, consist of 8-12, preferably 9-11, further preferred 9 or 10 nucleotides. An anticodon loop of 9 nucleotides is especially preferred.

The extended anticodon loop of the synthetic tRNA of the invention comprises two consecutive anticodon base triplets, which are configured to base-pair to two consecutive codon base triplets on an mRNA, the latter preferably being a targeted mRNA carrying a premature termination codon (PTC). One of the anticodon base triplets is configured to base-pair to a stop codon base triplet on the mRNA, whereas the neighbouring anticodon base triplet preferably is configured to base-pair to a sense codon preceding or following, i.e. 5' or 3' to the stop codon base triplet on the mRNA. The terms "preceding" or "following" relate to the direction of translation, i.e. the 5'-3' direction of the mRNA.

An example of an anticodon pair in the extended anticodon loop of the synthetic tRNA of the invention is UGCUCA (in 5'-3' direction, or ACUCGU in 3'-5' direction), matching with UGAGCA (5'-3') in the mRNA, where UCA is able to base-pair with the stop codon UGA, and UGC is able to base-pair with the codon GCA coding for alanine.

It is preferred that the two consecutive anticodon base triplets are asymmetrically arranged in the extended anticodon loop of the transfer RNA. "Asymmetrically arranged" in this context means that the 6 nt sequence composed of the two consecutive anticodon base triplets ("anticodon tandem") is, in a two-dimensional representation of the anticodon arm, arranged offset from an imaginary symmetry axis longitudinally traversing through the stem of the anticodon loop and extended in the direction of the anticodon loop (see also FIG. 2). For example, the anticodon tandem may be arranged within the anticodon loop such that four of the six nucleotides forming the anticodon tandem lie to one side of the axis, and the other two nucleotides lie on the other side of the axis. In other words, within the anticodon loop, the number of nucleotides flanking the anticodon tandem to the 3'-end and the 5'-end of the tRNA is not the same. There may be more nucleotides within the anticodon loop flanking the anticodon tandem to the 3'-end than to the 5'-end, or vice versa. It is to be noted in this context that, for an asymmetric arrangement of the anticodon tandem in the anticodon loop, it is only required that the larger share of the anticodon tandem is arranged offset the axis, without it being necessary that this always involves whole nucleotides. In a symmetric arrangement the anticodon tandem would be arranged in a manner that three nucleotides would be on one side and three on the opposite side of the axis.

In a preferred embodiment of the synthetic transfer RNA of the invention the two consecutive anticodon base triplets are offset to the 3'-end of the synthetic transfer RNA, i.e. there are more nucleotides within the anticodon loop flanking the anticodon tandem to the 5'-end.

In a preferred embodiment of the invention, the synthetic transfer RNA is further optimized, i.e. structurally modified, to enhance translation readthrough. The tRNA of the invention is thus preferably structurally, that is in terms of its nucleotide sequence, so designed that the tRNA body is adapted to the specific anticodon tandem and/or anticodon loop used in order to result in a maximum readthrough in vivo. The tRNA may, for example, be further modified regarding the nucleotide composition of its components outside the anticodon arm, for example of its T-arm, D-arm or variable loop. The term "translation readthrough" relates to the synthesis of a complete protein from an mRNA having a premature stop codon (PTC) within its sequence, i.e. to the translation of an mRNA with a PTC beyond the PTC, such that a complete and functional protein results, although the protein may lack an amino acid compared to the wild type protein. The expression "enhance translation readthrough" relates to the synthesis of a higher share of complete proteins from an mRNA comprising a PTC in the presence of a further modified tRNA compared to the translation involving a tRNA, which has not been further modified.

In a preferred embodiment, the T-stem is modified to be composed of a first five nucleotide T-stem sequence AGGGG and a second five nucleotide T-stem sequence CCCCU, wherein the second T-stem sequence is complementary to the first T-stem sequence and is arranged, in 5'-3' direction in relation to the tRNA, after the T-loop. The T-arm thus has the structure 5'-AGGGG-(T-Loop)-CCCCU-3'. With reference to a canonical tRNA (see FIG. 3) the sequence AGGGG would occupy the positions 49 to 53 according to the standard consensus numbering of tRNAs, and the corresponding nucleotide sequence CCCCU (in 5'-3' direction) positions 61 to 65.

Further, the tRNA of the invention may, additionally or alternatively, be modified in the sequence of its D arm. The tRNA of the invention may, for example, be modified to have a D arm having the sequence GCGCAGCCUG-GUAGCGC (SEQ ID NO: 31). In a preferred embodiment, the tRNA of the invention has the T-stem sequence described above and the D arm sequence of SEQ ID NO: 31.

The variable loop of the tRNA of the invention may also be modified in order to enhance translation readthrough. The variable loop may be modified alone or together with the T-stem and/or D arm. For example, the variable loop of the natural tRNA$^{Sec}$ (Selenocysteine tRNA), given in SEQ ID NO: 54, UUGGGGCCGCGCGGUCCCGG), or a modified variant thereof, may be incorporated. A modified variant of the tRNA$^{Sec}$ V-loop may have a shortened or extended sequence, or a sequence wherein one or more nucleotides are replaced with other nucleotides.

The synthetic transfer RNA according to the invention may be aminoacylated, i.e. carrying an amino acid or a dipeptide at the end of its acceptor stem. Preferably, the tRNA is aminoacylated with an amino acid being encoded by a sense codon base-pairing with one of the anticodon pairs or with an amino acid being encoded by a codon mutated to a premature termination codon and base-pairing with the other anticodon pair. The synthetic tRNA of the invention can be chemically and/or enzymatically aminoacylated with a single amino acid or dipeptide. The loading of a tRNA with a dipeptide can be accomplished with methods known to those skilled in the art (see, for example, Maini R, Dedkova L M, Paul R, Madathil M M, Chowdhury S R, Chen S, Hecht S M, 2015, Ribosome-Mediated Incorporation of Dipeptides and Dipeptide Analogues into Proteins in Vitro, J. Am. Chem. Soc., 137, 11206-11209, doi 10.1021/jacs.5b03135). Engineered bacterial tRNA synthetases or RNA-based catalysts may, for example, be used to aminoacylate the tRNA with a dipeptide. A dipeptide is preferably composed of the amino acids encoded by the codon pair corresponding to the anticodon pair present in the synthetic tRNA. The use of a synthetic tRNA aminoacylated with such a dipeptide would not only result in the intended suppression of the PTC and the production of a non-truncated protein, but in the production of a protein having the amino acid sequence of the wild-type protein.

In preferred embodiments, the synthetic transfer RNA of the invention has or comprises a) one of the sequences according to SEQ ID NO: 03-07, 09-17, 19-23, 25-30, 46-50 or 55-57, or b) a sequence having at least 90%, preferably at least 95%, 96%, 97%, 98% or 99% sequence identity with one of the sequences according to SEQ ID NO: 03-07, 09-17, 19-23, 25-30, 46-50 or 55-57, or c) a sequence of a) or b) above, wherein at least one of the nucleotides is replaced with a corresponding modified nucleotide. The term "replaced with a corresponding modified nucleotide" means that a unmodified nucleotide, e.g. a cytidine nucleotide (C), at a given position in a sequence, for example SEQ ID NO: 03, is replaced with a corresponding modified nucleotide, e.g. 2'-O-methylcytidine (cm), 3-methylcytidine (m3c) or 5-methylcytidine (m5c).

The synthetic transfer RNA of the invention may, for example, have or comprise a sequence containing more than 10, 20 or 30 modified nucleotides.

In preferred embodiments, the synthetic transfer RNA comprises a) an anticodon loop having a sequence selected from the group of sequences consisting of CUCAGUUAGA (SEQ ID NO: 51), CUCAGUUAAA (SEQ ID NO: 52), ACUCAGUUAG (SEQ ID NO: 53), CUCAGUUAG, CUCAGUUAA, CUCAGUUAU, AUCAGUUAG, and ACUCAGUUA, or b) an anticodon loop having a sequence selected from the group of sequences consisting of CUCAGUUAGA (SEQ ID NO: 51), CUCAGUUAAA (SEQ ID NO: 52), ACUCAGUUAG (SEQ ID NO: 53), CUCAGUUAG, CUCAGUUAA, CUCAGUUAU, AUCAGUUAG, and ACUCAGUUA, wherein at least one of the nucleotides is replaced with a corresponding modified nucleotide. Each of the sequences CUCAGUUAGA (SEQ ID NO: 51), CUCAGUUAAA (SEQ ID NO: 52), ACUCAGUUAG (SEQ ID NO: 53), CUCAGUUAG, CUCAGUUAA, CUCAGUUAU, AUCAGUUAG, and ACUCAGUUA contains the sequence of an extended anticodon loop (see Table 3 below) with 10 (SEQ ID NO: 51-53) or 9 nucleotides. Each anticodon loop contains the anticodon tandem CAGUUA and the transfer RNAs according to these embodiments are particularly useful as a medicament for use in cystic fibrosis, for example for correcting a Y1092X mutation in CFTR.

It is particularly preferred that a G-C or C-G pair is positioned at the end of the anticodon stem in direction of the anticodon loop, that is that the nucleotides of the anticodon stem flanking the anticodon loop form a G-C or C-G pair.

For clarification, it is noted that the synthetic transfer RNA of the invention may or may not be synthesized to contain any modified nucleotides. The synthetic transfer RNA of the invention may thus not contain any modified nucleotide. However, after entering a cell, one or more nucleotides of that synthetic tRNA may nevertheless be modified within the cell by the cellular enzymatic machinery. Consequently, a synthetic tRNA of the invention, which has been designed, synthesized and administered without any modified nucleotide, may, in a living cell, contain one or more modified nucleotides due to modifications the cell has made to them. In fact, it is preferred that the synthetic tRNA of the invention is synthesized and also administered without containing any modified nucleotides and to leave any modifications to the cell.

If a synthetic tRNA of the invention is synthesized with modified nucleotides, such that the tRNA already contains modified nucleotides prior to administration, it is preferred that the tRNA of the invention contains one or more of the following modified nucleotides (Table 1):

TABLE 1

Figure 3:
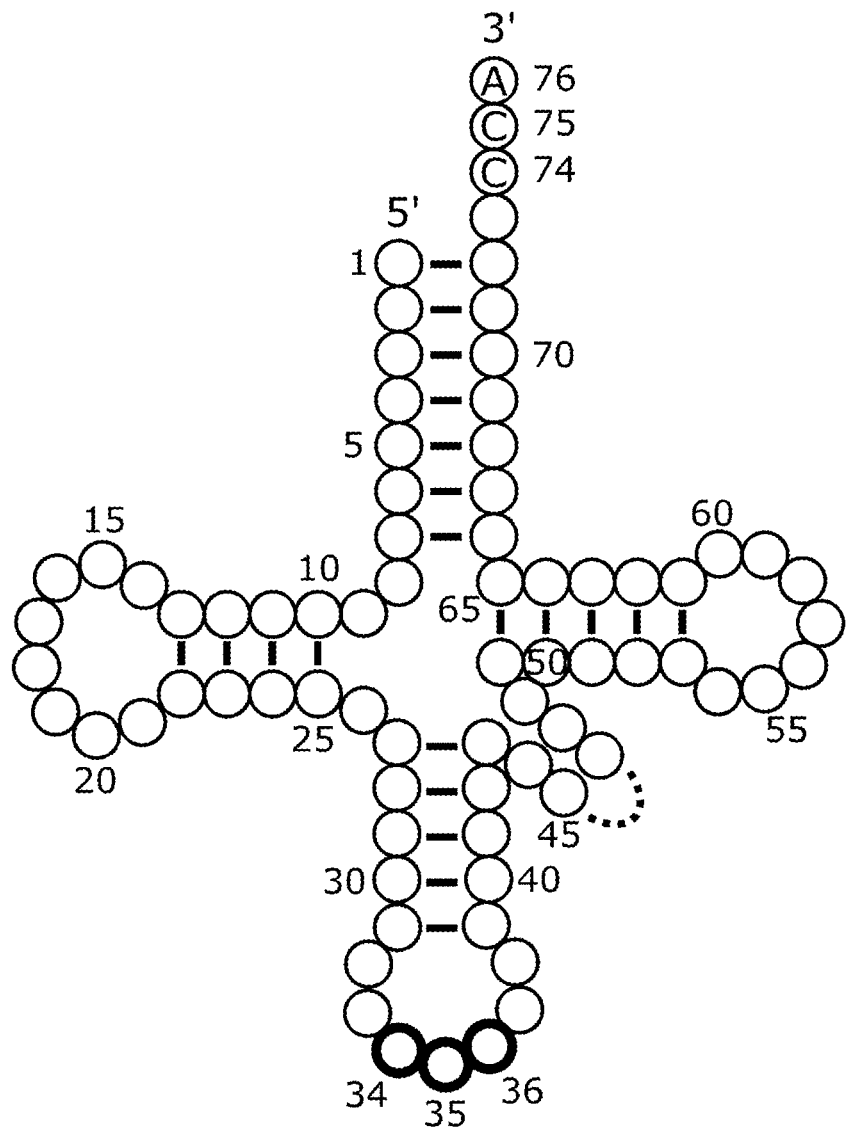

Possible modified nucleotides and positions within the tRNA (position numbering according to the specific tRNA numbering convention for a generalized "consensus" tRNA, see also FIG. 3)

| Position | Modification |
| --- | --- |
| 1 | Ψ |
| 4 | cm, am |
| 9 | m1g |
| 12 | ac4c |
| 16 | d |
| 17 | d |
| 18 | m2g |
| 20, 20a-b | d |
| 26 | m22g |
| 28 | Ψ |
| 29 | Ψ |
| 30 | Ψ |
| 32 | Ψ, 2'O-methylribose, cm |
| 34 | I, Ψ, m5c, cm, gm, 2'O-methylribose, q, mcm5u, ncm5u, ncm5um, mcm5s2u, |
| 35 | Ψ | m1g, 1-methylguanosine; am, 2'-O-methyladenosine; cm, 2'-O-methylcytidine; gm, 2'-O-methylguanosine; Ψ, pseudouridine; m2g, N2-methylguanosine; ac4c, N4-acetylcytidine; d,dihydrouridine; m22g, N2,N2-dimethylguanosine; m2g, N2-methylguanosine; I, inosine; m5c, 5-methylcytidine; mcm5u, 5-methoxycarbonylmethyluridine; mcm5s2u, 5-methoxycarbonyl-methyl-2-thiouridine; ncm5u, 5-carbamoylmethyluridine; ncm5um, 5-carbamoylmethyl-2'-O-methyluridine; q, queuosine; m5c, 5-methylcytidine.

In a further aspect the invention relates to the synthetic transfer RNA according to the first aspect of the invention for use as a medicament. The transfer RNA of the invention is especially useful for treating patients with a disease associated with a PTC causing the absence or dysfunction of a protein, in particular a disease at least partly caused by a nonsense mutation leading to premature cessation of translation of an mRNA. Examples for diseases, in which the tRNA of the invention may advantageously be employed are cystic fibrosis, neurofibromatosis type 1, Duchenne muscular dystrophy or Hurler syndrome. Suitable compositions or means for delivering tRNAs to a cell are known, and include viral vectors such as viral vectors like adeno-associated virus (AAV)-based viral vectors, encapsulation in or coupling to nanoparticles.

In a preferred embodiment, the synthetic transfer RNA according to the invention are designed for use as a medicament for treating cystic fibrosis, and the two consecutive anticodon base triplets of the extended anticodon loop have the sequence CAGUUA. The synthetic transfer RNA may, for example, comprise an anticodon loop having a) a sequence selected from the group of sequences consisting of CUCAGUUAGA (SEQ ID NO: 51), CUCAGUUAAA (SEQ ID NO: 52), ACUCAGUUAG (SEQ ID NO: 53), CUCAGUUAG, CUCAGUUAA, CUCAGUUAU, AUCAGUUAG, and ACUCAGUUA, or b) having a sequence selected from the group of sequences consisting of CUCAGUUAGA (SEQ ID NO: 51), CUCAGUUAAA (SEQ ID NO: 52), ACUCAGUUAG (SEQ ID NO: 53), CUCAGUUAG, CUCAGUUAA, CUCAGUUAU, AUCAGUUAG, and ACUCAGUUA, wherein at least one of the nucleotides is replaced with a corresponding modified nucleotide. It is particularly preferred that the synthetic transfer RNA has an extended anticodon loop composed of 9 nucleotides. An example of a suitable tRNA having an extended 9 nt nucleotide anticodon including the anticodon tandem CAGUUA is a transfer RNA with the sequence of SEQ ID NO: 6 or a sequence of SEQ ID NO: 6, wherein at least one of the nucleotides is replaced with a corresponding modified nucleotide.

The invention will be described by way of examples and the appended figures for illustrative purposes only.

FIG. 1 Schematic example of a synthetic tRNA of the invention and a targeted mRNA.

Figure 2:
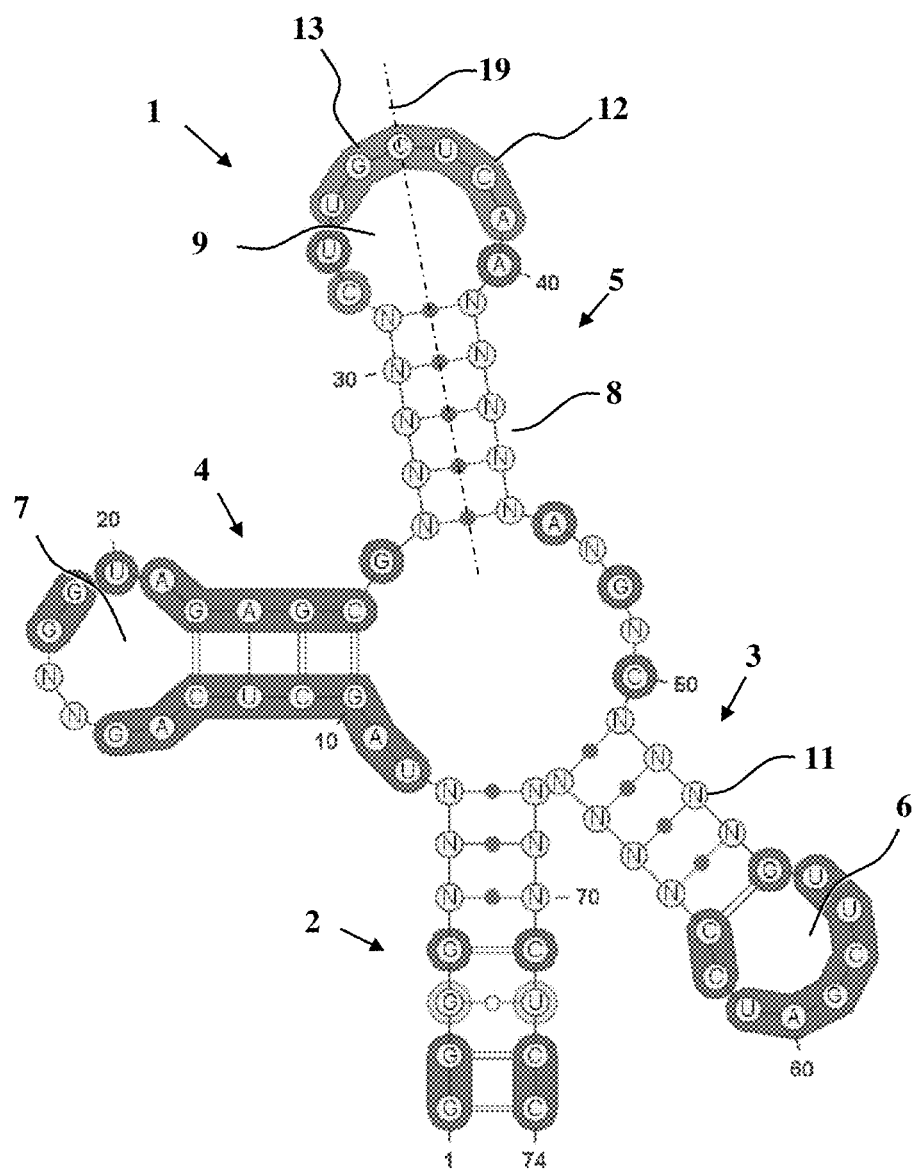

FIG. 2 Example embodiment of part of a synthetic Ala-tRNA of the invention. N=any nucleotide.

FIG. 3 Schematic drawing of a generalized "consensus" tRNA structure and its numbering according to tRNA numbering convention.

Figure 4:
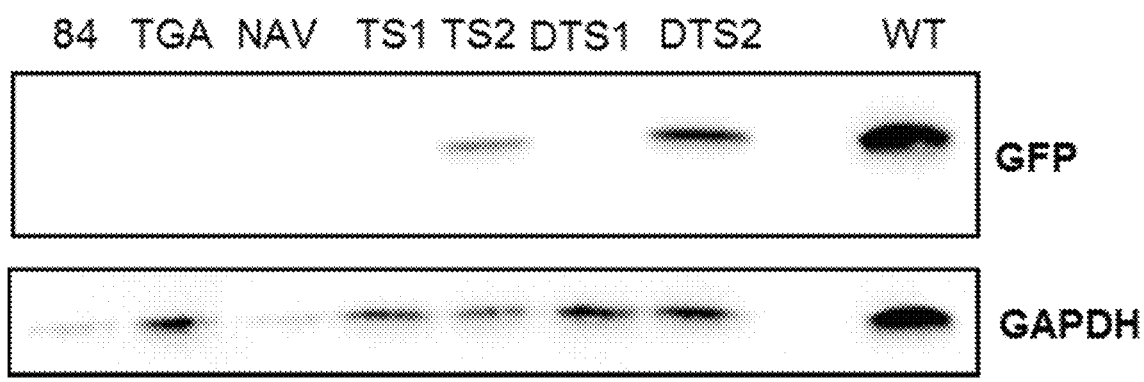
Figure 5A:
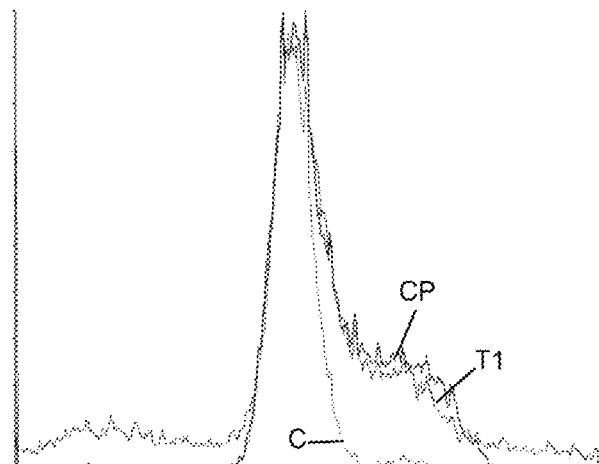
Figure 5A:
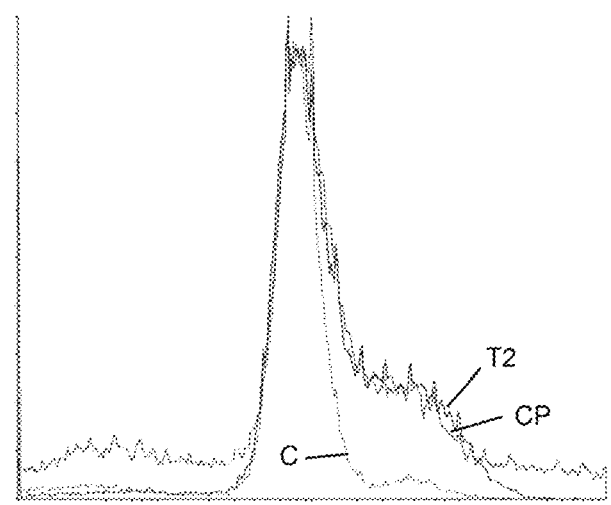
Figure 5B:
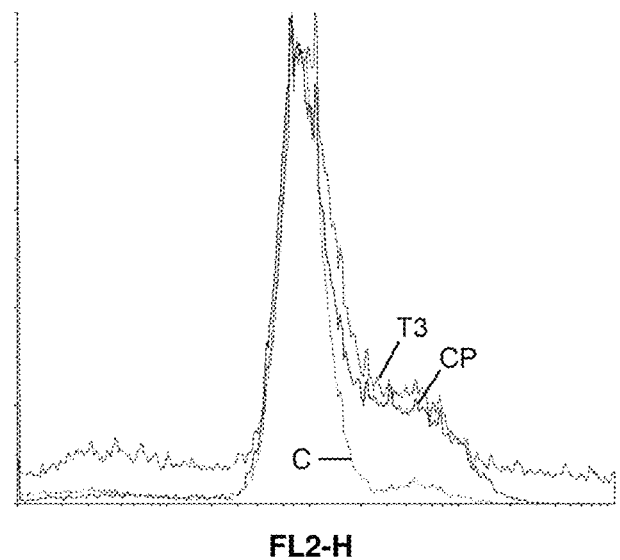
Figure 5B:
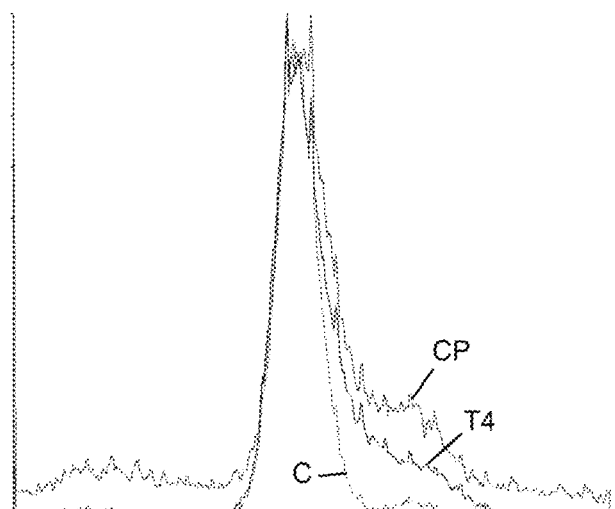
Figure 5C:
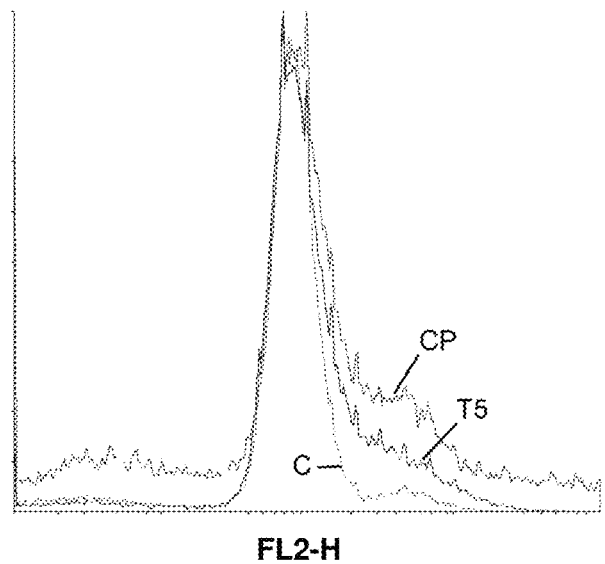
Figure 5C:
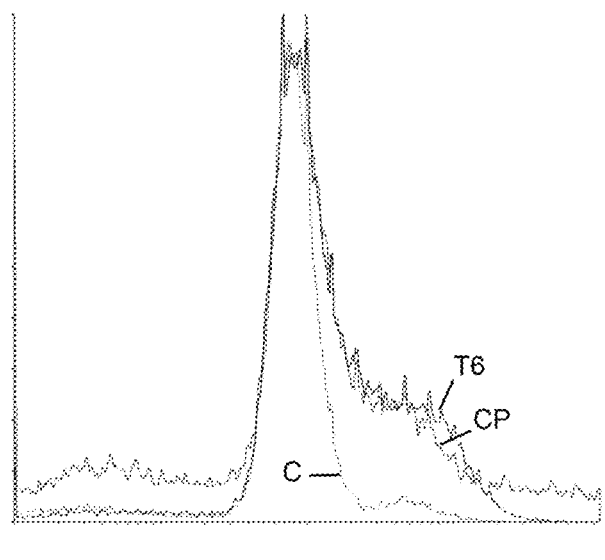
Figure 5D:
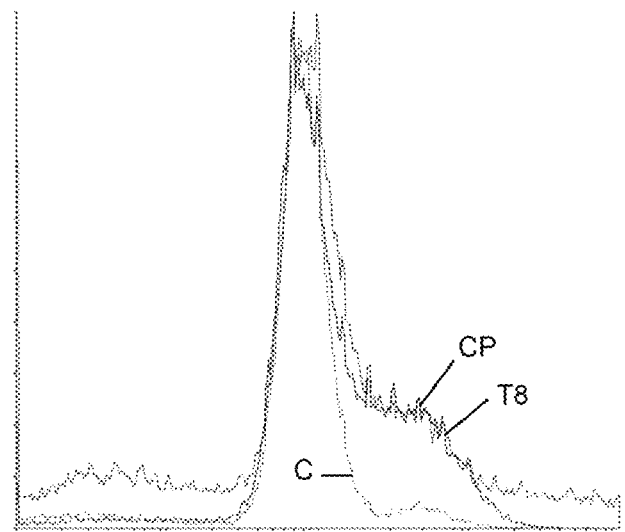
Figure 5D:
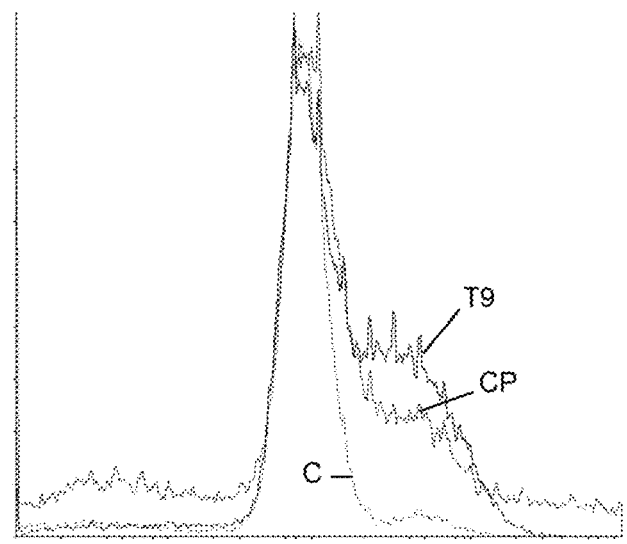

FIG. 4 Western blot showing GFP expression from a plasmid bearing a GFP coding sequence with a TGA stop codon using tRNA$^{Ala}$ variants with 3 nt anticodon pairing to the TGA stop codon (upper part of figure). Control (lower part of figure): expression of housekeeping GAPDH gene. WT=wild-type GFP; Negative controls: 84=cells expressing the plasmid without the GFP gene; TGA=GFP with a stop codon without suppressor tRNA; NAV=empty pBST NAV2 vector.

FIGS. 5A-D Results of experiments performed in HeLa cells for expression of the fluorescent mCherry protein from plasmid pECFP-C1 bearing an lint insert from the CFTR gene flanking the nonsense mutation Y1029X, sandwiched between CFP without stop codon and mCherry, using tRNA with extended anticodon loop. The mCherry expression was monitored by FACS detecting mCherry fluorescence. C=HeLa cells alone; CP=transformed pECFP1 bearing the reporter, no suppressor tRNA; T1-T6, T8-T9=with co-transformed pECFP1 bearing the reporter and corresponding suppressor tRNA with extended anticodon loop (T1-T6, T8-T9=tRNA-L1-6, tRNA-L8-9).

FIG. 1 shows a schematic example of a synthetic tRNA of the invention and a targeted mRNA. The synthetic tRNA 1 of the invention is composed of tRNA nucleotides 11 and has the common cloverleaf structure of natural tRNA comprising an acceptor stem 2 with the CCA tail 10, a T arm 3 with the TψC loop 6, a D arm 4 with the D loop 7 and an anticodon arm 5 with a five nucleotide stem portion 8 and the anticodon loop 9. An amino acid 14 is bound to the CCA tail 10 of the acceptor stem 2. The extended anticodon loop 9 consists of nine nucleotides 11 and contains two consecutive anticodon base triplets 12, 13. The first anticodon base triplet 12 (hatched circles) is able to base-pair to a first codon base triplet 17 (also hatched) on a targeted mRNA 15 composed of mRNA nucleotides 16. The second anticodon base triplet 13 (solid black circles) is able to base-pair to a second codon base triplet ~(also solid black) on the mRNA 15. The first codon base triplet 17 may be a premature termination codon (PTC) and the second codon base triplet 18 may code for an amino acid, e.g. alanine, or vice versa. A variable loop often found in naturally occurring tRNA between the T arm and the anticodon arm is missing here.

EXAMPLES

In silico design of a synthetic tRNA of the invention.

Unless otherwise indicated all sequences are written in the 5'-3' direction. In all sequences, if a minus sign (hyphen, "-") is used, this is for clarity only and does not refer to a physical nucleotide. It is a purely typographical convention to align sequences on a page. Further, unless expressly stated otherwise, bases are simply numbered sequentially, not according to the tRNA convention mentioned above.

First of all, a naturally occurring human Leu tRNA was modified only in its anticodon loop.

Original human tRNA-Leu (M2GAA) (genbank accession X04700.1; anticodon underlined), SEQ ID NO: 01:

GUCAGGAUGGCCGAGUGGUCUAAGGCGCCAGACU<u>NAA</u>GUUCUGGUCUCCG

GAUGGAGCGUGGGUUCGAAUCCCACUUCUGACACCA

The above naturally occurring tRNA contains, when isolated from a cell, modified bases in its sequence, which are represented in the above sequence by N or the corresponding unmodified bases. As an example, N at position 35 (corresponding to position 34 according to the specific tRNA numbering convention mentioned above) represents m22g (2,2-dimethylguanosine).

tRNAs were designed in order to be able to correct a mutation in CFTR leading to a stop codon (X) next to a codon coding for leucine (leu, L):

5'-CAGUUA-3' 6 nt anticodon pair complementary to the following codons:

3'-GUCAAU-5' mRNA sequence (5'-stop-leu-3') shall be recognized

In addition to a tRNA based on the natural tRNA modified in only one base in the normal anticodon, five tRNAs (designs 1.1 to 1.5) with an extended anticodon loop were designed. As mentioned above, modified nucleotides may or may not also be present in the modified sequences, i.e. the sequences given below for the designed tRNAs may contain one or more corresponding modified nucleotides instead of the unmodified bases. The number and kind of modified nucleotides may be the same or different from the ones in the natural tRNA template. Any unmodified nucleotide in a sequence for a synthetic tRNA of the invention may thus be replaced with a corresponding modified nucleotide. The symbols A, C, G or U in the below sequences for designed tRNAs may therefore represent an unmodified or any corresponding modified base. An A in a sequence may, for example, represent an adenine nucleotide (A) or a corresponding modified nucleotide, e.g. 1-methyladenosine (m1a). When synthesized in vitro, the tRNAs are preferably unmodified, but may be subsequently modified chemically and/or enzymatically in vitro. Once introduced or incorporated in a cell, the tRNAs, whether in vitro synthesized with unmodified or modified nucleotides, may be modified by the cell.

tRNA-Leu (UAA) with substituted base U at position 35 (34 according tRNA numbering convention), SEQ ID NO: 02

GUCAGGAUGGCCGAGUGGUCUAAGGCGCCAGACU<u>UAA</u>GUUCUGGUCUCCG

GAUGGAGCGUGGGUUCGAAUCCCACUUCUGACACCA

Design 1.1: tRNA-Leu CAGUUA anticodon pair (underlined), 10 nt anticodon loop, SEQ ID NO: 03

GUCAGGAUGGCCGAGUGGUCUAAGGCGCCAGACU<u>CAGUUA</u>GUUCUGGUCU

CCGGAUGGAGCGUGGGUUCGAAUCCCACUUCUGACACCA

Design 1.2: tRNA-Leu-CAGUUA anticodon, 9 nt anticodon loop (deleted C33, compared to design 1.1), SEQ ID NO: 04

GUCAGGAUGGCCGAGUGGUCUAAGGCGCCAGAU<u>CAGUUA</u>GUUCUGGUCUC

CGGAUGGAGCGUGGGUUCGAAUCCCACUUCUGACACCA

Design 1.3: tRNA-Leu-CAGUUA anticodon, 9 nt anticodon loop (deleted U34, compared to design 1.1), SEQ ID NO: 05

GUCAGGAUGGCCGAGUGGUCUAAGGCGCCAGAC<u>CAGUUA</u>GUUCUGGUCUC

CGGAUGGAGCGUGGGUUCGAAUCCCACUUCUGACACCA

Design 1.4: tRNA-Leu-CAGUUA anticodon, 9 nt anticodon loop (deleted G41, compared to design 1.1), SEQ ID NO: 06

GUCAGGAUGGCCGAGUGGUCUAAGGCGCCAGACU<u>CAGUUA</u>UUCUGGUCUC

CGGAUGGAGCGUGGGUUCGAAUCCCACUUCUGACACCA

Design 1.5: tRNA-Leu-CAGUUA anticodon, 9 nt anticodon loop (deleted U42, compared to design 1.1), SEQ ID NO: 07

GUCAGGAUGGCCGAGUGGUCUAAGGCGCCAGACU<u>CAGUUA</u>GUCUGGUCUC

CGGAUGGAGCGUGGGUUCGAAUCCCACUUCUGACACCA

The optimal anticodon loop length was 9 nt.

Starting from design 1.4 (CAGUUA anticodon, 9 nt anticodon loop (deleted G41)), further Leu tRNA (with 6 nt anticodon pair) were designed with less similarity to the naturally occurring tRNAs, based on the crystal structure from a tRNA-Leu from *Thermus thermophilus*: tRNA-Leu-CAG from *Thermus thermophilus* (3 nt anticodon, sequence is from RCSB Protein Data Bank identifier 2bte.b; any modified nucleotides present in the sequence are represented by their respective unmodified nucleotides).

SEQ ID NO: 08
GCCGGGGUGGCGGAAUGGGUAGACGCGCAUGACUCAGGAUCAUGUGCGCA

AGCGUGCGGGUUCAAGUCCCGCCCCCGGCACCA

This resulted in the design of the following tRNA-Leu-CAGUUA (Leu-Stop) having 6 nt anticodon pairs based on design 1.4 (9 nt anticodon loop) above:

Design 2.1 (SEQ ID NO: 09):
GGCAGGCUGAGGGAGAUGGUCAACCUAGCCAGCUCAGUUAGCUGGCUCUC

CGGAUGGAGCGUGGCUUCGAAUGCCACGCCUGCCACCA

Design 2.2 (SEQ ID NO: 10):
GACAGGCUGAGGGAGAUGGUCAACCUAGCAGCCUCAGUUAGGCUGCUCUC

CGGAUGGAGCGUGGCUUCGAAUGCCACGCCUGUCACCA

Design 2.3 (SEQ ID NO: 11):
GCCAGCCUGAGGGAGAUGGUCAACCUAGCCAGCUCAGUUAGCUGGCUCUC

CGGAUGGAGCGUGGCUUCGAAUGCCACGGCUGGCACCA

Design 2.4 (SEQ ID NO: 12):
GGCAGCCUGAGGGAGAUGGUCAACCUAGCAGCCUCAGUUAGGCUGCUCUC

CGGAUGGAGCGUGGCUUCGAAUGCCACGGCUGCCACCA

Design 2.5 (SEQ ID NO: 13):
GCCAGCCUGAGGGAGAUGGUCAACCUAGGUGCCUCAGUUAGGCACCUCUC

CGGAUGGAGCGUGGCUUCGAAUGCCACGGCUGGCACCA

Design 2.6 (SEQ ID NO: 14):
GCCAGCCUGAGGGAGAUGGUCAACCUACUGGACUCAGUUAGUCCAGUCUC

CGGAUGGAGCGUGGCUUCGAAUGCCACGGCUGGCACCA

Design 2.7 (SEQ ID NO: 15):
GCCAGCCUGAGGGAGAUGGUCAACCUACCGGACUCAGUUAGUCCGGUCUC

CGGAUGGAGCGUGGCUUCGAAUGCCACGGCUGGCACCA

Design 2.8 (SEQ ID NO: 16):
GCCAGCCUGAGGGAGAUGGUCAACCUACCUGCCUCAGUUAGGCAGGUCUC

CGGAUGGAGCGUGGCUUCGAAUGCCACGGCUGGCACCA

Design 2.9 (SEQ ID NO: 17):
GCCAGGCUGAGGGAGAUGGUCAACCUAGCUCACUCAGUUAGUGAGCUCUC

CGGAUGGAGCGUGGCUUCGAAUGCCACGCCUGGCACCA

Again, any modified nucleotide present in the natural sequence taken as a template for the design of the synthetic tRNAs may or may not also be present in the designed sequences. The designed tRNAs above thus may or may not contain one or more corresponding modified nucleotides instead of the unmodified bases.

For the correction of a further stop mutation (at position 553) in the CFTR gene (R553X), mutating the wild-type codon CGA coding for arginine (R), and flanked by codons coding for glutamine (Q) and alanine (A), to a stop codon (TGA on gene level)

```
CAA CGA GCA     (wildtype nucleotide sequence)

Q   R   A      (wildtype amino acid sequence)

CAA TGA GCA     (mutated nucleotide sequence)

Q   X   A      (mutated nucleotide sequence)
``` the tRNA was designed to have a 6 nt anticodon pair (UGCUCA) and to be aminoacylated with alanine (Ala, A), i.e. to have the identity of a Ala-tRNA. Ala is the amino acid following the stop codon (in 3' direction of the mRNA).

The goal was to design a tRNA that would be able to read through a stop codon and deliver a Ala to the protein being translated (read through a premature stop codon caused by mutation which would otherwise lead to a truncated protein).

5'-UGCUCA-3' 6 nt anticodon pair complementary to the two codons below
3'-ACGAGU-5' mRNA sequence (5-Stop-Ala-3'; XA) to be recognised Similar to the Leu-tRNAs at first a natural human Ala-tRNA was minimally changed, i.e. only in the anticodon loop. Again, any modified nucleotides in the sequence are represented by their unmodified equivalents, and the synthetic tRNAs designed based on the natural tRNA may or may not contain all or part of the modified nucleotides of the natural sequence. The designed tRNAs may also contain more or other modified nucleotides than the ones present in the naturals sequence and/or at another position.

tRNA-Ala-AGC (SEQ ID NO: 18), without free 3' end ACCA:
GGGGAAUUAGCUCAAAUGGUAGAGCGCUCGCUUAGCAUGCGAGAGGUAGC

GGGAUCGAUGCCCGCAUUCUCC

Design 3.1 (10 nt anticodon loop) (SEQ ID NO: 19)
GGGGAAUUAGCUCAAAUGGUAGAGCGCUCGCUUUGCUCAAUGCGAGAGGU

AGCGGGAUCGAUGCCCGCAUUCUCCACCA

Design 3.2 (9 nt anticodon loop) (SEQ ID NO: 20)
GGGGAAUUAGCUCAAAUGGUAGAGCGCUCGCUUGCUCAAUGCGAGAGGUA

GCGGGAUCGAUGCCCGCAUUCUCCACCA

Design 3.3 (9 nt anticodon loop) (SEQ ID NO: 21)
GGGGAAUUAGCUCAAAUGGUAGAGCGCUCGCUUUGCUCAUGCGAGAGGUA

GCGGGAUCGAUGCCCGCAUUCUCCACCA

Design 3.4 (9 nt anticodon loop) (SEQ ID NO: 22)
GGGGAAUUAGCUCAAAUGGUAGAGCGCUCGCUUUGCUCAAGCGAGAGGUA

GCGGGAUCGAUGCCCGCAUUCUCCACCA

Experiments showed that both 10 nt and 9 nt anticodon loop tRNAs formed a secondary structure corresponding to naturally occurring tRNA, and the single-stranded CCA tails were intact. All tRNAs could be aminoacylated.

Starting from design 1.4 of the Ala-tRNA further Ala-tRNA were designed, such that the tRNA body did not correspond to the natural human tRNA.

tRNA-Ala-UGCUCA-design 3.4
(SEQ ID NO: 22)
GGGGAAUUAGCUCAAAUGGUAGAGCGCUCGCUUUGCUCAAGCGAGAGGUA

GCGGGAUCGAUGCCCGCAUUCUCCACCA

A generalized secondary structure of the designed tRNA is depicted in FIG. 2 (sequence shown in the figure given in SEQ ID NO: 24). Reference numbers correspond to those used in FIG. 1. The free 3' end including the CCA tail portion is not shown. Also shown in FIG. 2 is the asymmetric arrangement of the two consecutive anticodon base triplets ("anticodon tandem") 13 in the extended anticodon loop 9 in relation to an imaginary symmetry axis 19 longitudinally traversing through the stem 8 of the anticodon arm 5 and extended in the direction of the anticodon loop 9. The anticodon tandem 13 is arranged offset towards the 3' end of the tRNA.

The sequence of the tRNA based on the Ala-tRNA and having a 9 nt anticodon loop with a 2×3 nt anticodon (FIG. 2) and including the 3' end portion is as follows (SEQ ID NO: 23):

GGGGNNNUAGCUCAGNNGGUAGAGCGNNNNNCU<u>UGCUCA</u>ANNNNNANGNC

NNNNGUUCGAUCCNNNNNNNNCUCCACCA

As already mentioned in connection with other synthetic tRNAs of the invention, the symbols G, C, A or U may represent the unmodified or any corresponding modified base. The above designed tRNA may thus contain one or more modified nucleotides.

N stands for any of the bases A, C, G or U, or any modified base, given that the base doesn't violate the base pairing as given in FIG. 2. The allowed base pairs are G-C, C-G, A-U, U-A, and wobble base pairs like G-U, U-G, I-U, U-I, I-A, A-I and I-C, C-I.

FIG. 3 depicts an example of a tRNA numbered according to the conventional numbering applied to a generalized "consensus" tRNA, beginning with 1 at the 5' end and ending with 76 at the 3' end. In such a "consensus" tRNA the nucleotides of the natural anticodon triplet is always at positions 34, 35 and 36, regardless of the actual number of previous nucleotides. Other than the tRNA shown here a tRNA may, for example, also contain additional nucleotides between positions 1 and 34, e.g. in the D loop. Additional nucleotides may be numbered with added alphabetic characters, e.g. 20a, 20b etc. Modified nucleotides, as e.g. listed in Table 1 above, may be present in the sequence.

Optimizing the tRNA body sequence for efficient readthrough

Different tRNAs (n1-n6, SEQ ID NO: 33-38) based on a natural human tRNA$^{Ala}$ were synthesized in vitro. All tRNAs had the same non-extended anticodon loop containing an anti-stop-codon, that is a anticodon complementary to a stop codon. For this purpose, oligonucleotides having the tRNA sequences were ligated with the T7 promotor sequence (SEQ ID NO: 32), and the tRNAs were produced in a T7-based in vitro transcription system. Subsequently, the tRNAs were purified using polyacrylamide gel electrophoresis (PAGE).

The template for T7-promoter driven transcription of designed tRNAs was generated by annealing and primer extension of two overlapping DNA oligonucleotides (commercially available) covering the whole length of each tRNA including the T7 promoter sequence (5'-TAATACGACTCACTATA-3', SEQ ID NO: 32). Both oligonucleotides were denatured for 2 min at 95° C. and annealed in their partial overlapping area by incubating for 3 min at room temperature in 0.2 M Tris-HCl (pH 7.5). To fill up the DNA templates, that is to extend the nucleotide chains and form fully double-stranded DNA (dsDNA), 0.4 mM dNTPs, 4 U/μL RevertAid Reverse Transcriptase (RT, Thermo Fisher) and 1× RT buffer were added to the annealed oligonucleotides and reactions were incubated for 40 min at 37° C. The DNA template was purified with phenol/chloroform.

The in vitro T7-driven transcription of tRNAs was performed in two different scales, dependent on the follow-up experiment. For in vitro analysis of the tRNA integrity we used 1 μg template DNA in 40 mM Tris-HCl (pH 7.0, containing 6 mM MgCl$_2$, 10 mM DTT, 10 mM NaCl, 2 mM spermidine, 2 mM NTPs, 1.25-5 mM GMP) and 30 U T7 RNA polymerase (Thermo Fisher) overnight at 37° C. tRNAs were precipitated with ethanol, separated on 10% denaturing polyacrylamide gels and eluted overnight at 4° C. with 50 mM potassium acetate (KOAc), 200 mM KCl pH 7.0 at constant shaking (1000 rpm). tRNAs were recovered by ethanol precipitation and resuspended in DEPC-H$_2$O (DEPC=diethylpyrocarbonate).

For transfections into eukaryotic cells since larger amounts are needed, 20 μg template were mixed with 100 mM of each NTP, 100 mM GMP, 1.2 U T7 RNA polymerase (Thermo Fisher) in 1× transcription buffer and incubated overnight at 37° C. The tRNAs were purified as described above, resuspended in DEPC-H$_2$O and stored at −80° C. for further use.

In order to check the folding and the integrity of the CCA ends, the tRNA were incubated with a fluorophore-labelled oligonucleotide in a ratio of 1:1 for 1 h at 25° C., and subsequently separated via PAGE. Fluorescent labelling was performed by ligating a Cy3-labeled RNA/DNA stem-loop oligonucleotide to the common 3'-NCCA ends of tRNAs as described earlier (Czech A, Wende S, Mörl M, Pan T, Ignatova Z, 2013, Reversible and rapid transfer-RNA deactivation as a mechanism of translational repression in stress, PLoS Genet. 2013 9(8):e1003767. doi: 10.1371/journal.pgen.1003767). The tRNAs labelled with the fluorescing oligonucleotide could be visualised in a fluorescence imager and migrate slower than non-labelled tRNAs. The designed tRNAs n1 to n5 were compared to controls: native tRNA$^{Ala}$ (GGC) (SEQ ID NO: 41), native tRNA$^{Ala}$ (UGC) (SEQ ID NO: 42), native tRNA$^{Ala}$ in which only the anticodon was replaced with an anti-stop codon tRNA$^{Ala}$ (UCA), SEQ ID NO: 41, and n6 (no tertiary interactions in the design), SEQ ID NO:38. The ratio of labelled (ligated) to non-labelled (non-ligated) tRNAs gives the ligation efficiency (table 2).

TABLE 2

| Ligation efficiency of designed tRNA compared to controls. | | |
|---|---|---|
| tRNA species | SEQ ID NO: | Ligation efficiency |
| tRNA$^{Ala}$ (n1) | 33 | ~20% |
| tRNA$^{Ala}$ (n2) | 34 | ~15% |
| tRNA$^{Ala}$ (n3) | 35 | ~15% |
| tRNA$^{Ala}$ (n4) | 36 | ~17% |
| tRNA$^{Ala}$ (n5) | 37 | ~14% |
| tRNA$^{Ala}$ (n6) | 38 | ~16% |
| tRNA$^{Ala}$ (GGC) | 39 | ~16% |
| tRNA$^{Ala}$ (UGC) | 40 | ~17% |
| tRNA$^{Ala}$ (UCA) | 41 | ~14% |

The designed tRNAs were tested for correct folding and aminoacylation. tRNA folding and aminoacylation reactions were performed using 1 mM alanine and 1 μM of E. coli alanyl-tRNA synthetase. Aminoacylated tRNAs were precipitated with ethanol and directly dissolved in 2× acidic RNA loading dye (0.1 M NaOAc pH 4.8, containing 8M urea, 5% glycerol, 0.025% bromophenol blue, 0.025% xylene cyanol FF). Charged and uncharged tRNA fractions were separated on denaturing acidic PAGE (6.5%, 8 M urea, 0.1M NaOAc pH 5.0) at 4° C. tRNAs were visualized by SYBR® gold (Invitrogen) staining.

All in-vitro-designed tRNAs were aminoacylated to a degree similar to the native tRNA$^{Ala}$ except n2, which was not acylated.

A GFP readthrough assay was used to test whether designed tRNA containing a stop codon in the non-extended anticodon loop are translationally active or not. For this purpose, a translational system was used comprising the coding sequence of green fluorescent protein (GFP). The codon coding for the 28$^{th}$ amino acid in the GFP was replaced with a stop codon. With the stop codon, GFP is normally not expressed. If, however, a designed suppressor tRNA having an anticodon complementary to the stop codon pairs to this codon, GFP is expressed. Its expression can be detected by either a fluorescence activated cell sorting (FACS) apparatus or by Western blot.

It is to be noted that, in this assay, only one codon (triplet) in the GFP coding sequence was replaced with a stop codon in order to avoid the green fluorescent protein not folding. Nevertheless, the method is fast and can be used to determine the effects of modifications to the tRNA body (see below). For the further experiments, the anticodon loop of the tRNAs was not changed. Only the natural anticodon of Ala-tRNA was converted into an antistop codon.

Two systems were used: a) an in vitro translation system and b) expression in E. coli. In case of the in vitro translation system expression was measured by Western blot, in case of the use of E. coli, Western blot and occasionally FACS was applied. Since the designed tRNAs share the same architecture for translation and loading, their translational ability is independent of the system and they can be used for in vitro expression as well as in vivo expression in prokaryotes or eukaryotes.

For in vitro translation a commercially available system was used (Promega). In the in vitro translation system, the tRNA was first transcribed in vitro and added 1:10 to the plasmid DNA (GFP with PTC, i.e. stop codon). After 1 hr at 30° C., the reaction mixture was separated by PAGE and an aliquot was detected with GFP antibodies.

For the in vivo expression system, designed tRNAs were cloned into the pBST NAV2 vector under the 1pp promoter (Meinnel T, Blanquet S J, 1995, Maturation of pre-tRNA (fMet) by Escherichia coli RNase P is specified by a guanosine of the 5'-flanking sequence, Biol Chem. 270: 15908-14). XL1-blue cells were co-transformed with pBAD33 plasmid bearing wildtype GFP or PTC GFP variants and tRNA-expressing pBST NAV2 vector and grown in LB medium at 37° C. Growth curves were recorded at OD600 nm. The expression of the GFP variants was induced at $OD_{600\ nm}=0.4$ with 0.05% L-arabinose. Cells were harvested at $OD_{600\ nm}=1.0$ and the GFP expression was monitored by immunoblotting using anti-GFP antibodies. The expression is compared to the housekeeping GAPDH gene. In parallel, cells were harvested, washed and resuspended in PBS buffer and subjected to fluorescence measurements in bulk using a microtiter plate reader (Tecan GENios) with 485 nm excitation and 535 nm emission filter, or subjected to flow cytometry on FACS Calibur (Becton Dickinson).

For the readthrough assay, designed variants of the n1 tRNA$^{Ala}$ variant having an anti-stop-codon in its non-extended anticodon loop to pair to the TGA stop codon were used, which were further modified in their T-stem or in both their T-stem and D arm in order to determine the effect of modifications to the T-stem and D arm for promoting translation readthrough. The in vivo translation system described above was used for this purpose. Translation of Glyceraldehyde 3-phosphate dehydrogenase (GAPDH) and wild-type GFP (without PTC) were used as a control.

The tRNA modified in their T-stem were designated TS1 (SEQ ID NO: 42) and TS2 (SEQ ID NO: 43), the tRNA modified in their T-stem and additionally in their D arm were designated DTS1 (SEQ ID NO: 44) and DTS2 (SEQ ID NO: 45)

TS1 (SEQ ID NO: 42); underlined: anticodon; bold: T-stem
GGGGCGGUAGCUCAGAAGGGAGAGCAGCGGCCUUCAGAGCCGCGAGACUG

CCCUUCGAUUGGGCACCGCUCCACCA

TS2 (SEQ ID NO: 43); underlined: anticodon; bold: T-stem
GGGGCGGUAGCUCAGAAGGGAGAGCAGCGGCCUUCAGAGCCGCGAGACAG

GGGUUCGAUUCCCCUCCGCUCCACCA

DTS1 (SEQ ID NO: 44); underlined: anticodon; bold: T-stem, italics = D arm
GGGGCGGUA*GCGCAGCCUGGUAGCGC*AGCGGCCUUCAGAGCCGCGAGACU

GCCCUUCGAUUGGGCACCGCUCCACCA

DTS2 (SEQ ID NO: 45); underlined: anticodon; bold: T-stem, italics = D arm
GGGGCGGUA*GCGCAGCCUGGUAGCGC*AGCGGCCUUCAGAGCCGCGAGACA

GGGGUUCGAUUCCCCUCCGCUCCACCA

The tRNA TS2 (SEQ ID NO: 43) modified to have a T-stem nucleotide sequence of AGGGG (positions 49 to 53, numbering according to tRNA convention) and CCCCU (positions 61 to 65, numbering according to tRNA convention), i.e. the following T-stem structure

3'-UCCCC-5'

5'-AGGGG-3' showed readthrough (see TS2 in FIG. 4). It is to be noted that the T-loop would be between the G at the 3' end of the AGGGG sequence and the C at the 5' end of the UCCCC sequence. The corresponding T arm would thus have the structure 5'-AGGGG-(T-Loop)-CCCCU-3'.

In order to test the effect of a modification of other structures of the tRNA body on translation readthrough, the above-described tRNA with modified T-stem (TS1 and TS2) were further modified in that the D-arm was replaced with the D-region of the E. coli tRNA$^{Pro}$. The modified tRNA were designated DTS1 (SEQ ID NO: 44) and DTS2 (SEQ ID NO: 45). The tRNA DTS2 (SEQ ID NO: 45) modified in its T-stem and its D arm promoted a higher readthrough than the tRNA only modified in its T-stem (see DTS2 in FIG. 4).

Using tRNA$^{Leu}$ for correcting Y1092X mutation in CFTR

A modified tRNA$^{Leu}$ was used to correct the Y1092X mutation in CFTR, resulting from a change of C at position 3276 to A or G in the CFTR gene:

```
Natural CFTR sequence:      TTGTACCTG

Mutated sequence (C3276A):  TTGTAACTG
```

The natural tRNA$^{Leu}$ (see SEQ ID NO: 1) was used as a template in order to design modified tRNAs having an anticodon tandem of the sequence CAGUUA in their anticodon loop. The designed tRNAs could be aminoacylated in vivo with leucine (Leu). The identity elements for the Leucyl-tRNA synthetase were unchanged.

To test whether the designed tRNAs would function in a translation system, a sandwich construct was used, comprising a short sequence containing the mutated CFTR sequence (UUGUAACUG) sandwiched between two fluorescent proteins, namely yellow fluorescent protein (CFP) and mCherry. CFP had no stop codon and was extended with an 11 nucleotide long insert being a piece of the gene to be repaired (here CFTR around the mutation Y1029X) and containing a stop codon. The tRNA anticodon loops were correspondingly extended in order to pair to six consecutive nucleotides. After the insert containing a stop codon, mCherry was cloned without an initial codon (coding for the amino acid Met), so that no independent translation of mCherry could take place. In the bicisctronic reporter system, CFP is always expressed up to the stop codon of the mutation, while mCherry is only expressed when readthrough takes place. This expression can be detected by either a fluorescence activated cell sorting (FACS) apparatus or by Western blot. A plasmid without insert was used as a control.

For studying tRNA suppression in HeLa cells, HeLa cells were maintained at 37° C., 5% CO2 in DMEM media supplemented with 10% FBS (fetal bovine serum) and 1% glutamine (GIBCO). One day prior to co-transfection ~200, 000 cells were seeded in 6-well plates. The transfection mix included 600 ng reporter plasmid encoding CFP-PTC-mCherry cloned in the pECGFP-C1 backbone, 150 ng suppressor tRNAs, 5 μl Lipofectamine 2000 (ThermoFisher Scientific, USA) in 200 μL Optimem medium (Gibco). Cells were incubated with transfection mix for 6 hours. Thereafter, the medium was exchanged with fresh medium. After 24 hours, the cells were washed with 1×PBS and analysed by FACS Calibur (Becton Dickinson). Analysis was performed by counting 50000 events, FSC Voltage E00 and 1.60 Amp Gain and using 400 nm wavelength for CFP and 520 nm for mCherry detection.

The following tRNA variants (anticodon tandem underlined) were tested (see also Table 3):

tR-L1
(SEQ ID NO: 46)
GUCAGGAUGGCCGAGUGGUCUAAGGCGCCACCUCAGUUAGAGUCUGGUCUC

CGGAUGGAGCGUGGGUUCGAAUCCCACUUCUGACACCA tR-L2
(SEQ ID NO: 47)
GUCAGGAUGGCCGAGUGGUCUAAGGCGCCACCUCAGUUAAAGUCUGGUCUC

CGGAUGGAGCGUGGGUUCGAAUCCCACUUCUGACACCA tR-L3 = tRNA Leu Design 1.1
(SEQ ID NO: 3)
GUCAGGAUGGCCGAGUGGUCUAAGGCGCCAGACUCAGUUAGUUCUGGUCUC

CGGAUGGAGCGUGGGUUCGAAUCCCACUUCUGACACCA tR-L4
(SEQ ID NO: 48)
GUCAGGAUGGCCGAGUGGUCUAAGGCGCCACCUCAGUUAGGUCUGGUCUCC

GGAUGGAGCGUGGGUUCGAAUCCCACUUCUGACACCA tR-L5
(SEQ ID NO: 49)
GUCAGGAUGGCCGAGUGGUCUAAGGCGCCACCUCAGUUAAGUCUGGUCUCC

GGAUGGAGCGUGGGUUCGAAUCCCACUUCUGACACCA tR-L6
(SEQ ID NO: 50)
GUCAGGAUGGCCGAGUGGUCUAAGGCGCCACCUCAGUUAUGUCUGGUCUCC

GGAUGGAGCGUGGGUUCGAAUCCCACUUCUGACACCA tR-L8 = tRNA Leu Design 1.2
(SEQ ID NO: 4)
GUCAGGAUGGCCGAGUGGUCUAAGGCGCCAGAUCAGUUAGUUCUGGUCUC

CGGAUGGAGCGUGGGUUCGAAUCCCACUUCUGACACCA tR-L9 = tRNA Leu Design 1.4
(SEQ ID NO: 6)
GUCAGGAUGGCCGAGUGGUCUAAGGCGCCAGACUCAGUUAUUCUGGUCUC

CGGAUGGAGCGUGGGUUCGAAUCCCACUUCUGACACCA

TABLE 3 tRNA variants tested for suppression. Bold and underlined: anticodon tandem. Numbering according to tRNA numbering convention.

| tRNA$^{Leu}$ variant | SEQ ID NO: | Anticodon loop nt | Anticodon loop sequence | SEQ ID NO: | Anticodon tandem |
|---|---|---|---|---|---|
| | | | 32-33-34-35-36-37-38 | | |
| tR-L1 | 46 | 10 nt | C-U-C-A-G-U-U-A-G-A | 51 | CAGUUA |
| tR-L2 | 47 | 10 nt | C-U-C-A-G-U-U-A-A-A | 52 | CAGUUA |
| tR-L3 | 3 | 10 nt | A-C-U-C-A-G-U-U-A-G | 53 | CAGUUA |
| tR-L4 | 48 | 9 nt | C-U-C-A-G-U-U-A-G | | CAGUUA |
| tR-L5 | 49 | 9 nt | C-U-C-A-G-U-U-A-A | | CAGUUA |
| tR-L6 | 50 | 9 nt | C-U-C-A-G-U-U-A-U | | CAGUUA |
| tR-L8 | 4 | 9 nt | A-U-C-A-G-U-U-A-G | | CAGUUA |
| tR-L9 | 6 | 9 nt | A-C-U-C-A-G-U-U-A | | CAGUUA |

The sequences of the tRNA variants are given in SEQ IDs NO: 3, 4, 6, 46-50, the sequences of the 10 nt anticodon loops in Table 3 are presented in SEQ ID NO: 51-53.

All modified tRNA were tested for readthrough (see FIG. 5). The most promising tRNA was tRL9 (T9, FIG. 5D, bottom, SEQ ID NO: 6) which led to significant read through and detection of mCherry. Further, asymmetric positioning of the anticodon tandem with total size of the anticodon loop of 9 nt were the most effective.

The invention claimed is:

1. A synthetic transfer RNA comprising an extended anticodon loop with two consecutive anticodon base triplets configured to base-pair to two consecutive codon base triplets on an mRNA, wherein the first anticodon base triplet or the second anticodon base triplet is configured to base-pair to a stop codon base triplet on the mRNA, the synthetic transfer RNA having or comprising a sequence having at least 90% sequence identity with one of the sequences according to SEQ ID NO: 03-07, 09-17, 19-23, 25-30, 46-50 and 55-57, wherein the sequences are identical or at least one of the nucleotides is replaced with a corresponding modified nucleotide.

2. A method for treating a disease which is at least partly caused by a nonsense mutation leading premature cessation of the translation of an mRNA, the method comprising administering a synthetic transfer RNA according to claim 1 to a patient with the disease.

3. A medicament for treating cystic fibrosis, the medicament comprising a synthetic transfer RNA comprising an extended anticodon loop with two consecutive anticodon base triplets configured to base-pair to two consecutive codon base triplets on an mRNA,
wherein the first anticodon base triplet or the second anticodon base triplet is configured to base-pair to a stop codon base triplet on the mRNA,
wherein the two consecutive anticodon base triplets of the extended anticodon loop have the sequence CAGUUA,
wherein the synthetic transfer RNA comprises (i) an anticodon loop having a sequence of ACUCAGUUA, or (ii) an anticodon loop having a sequence of ACUCAGUUA, wherein at least one of the nucleotides is replaced with a corresponding modified nucleotide,
wherein the extended anticodon loop is composed of 9 nucleotides, and
wherein the transfer RNA comprises (a) a sequence of SEQ ID NO: 6 or (b) a sequence of SEQ ID NO: 6, wherein at least one of the nucleotides is replaced with a corresponding modified nucleotide.

* * * * *

SEQUENCE LISTING

<160> NUMBER OF SEQ ID NOS: 57

<210> SEQ ID NO 1
<211> LENGTH: 86
<212> TYPE: RNA
<213> ORGANISM: Homo sapiens
<220> FEATURE:
<221> NAME/KEY: modified_base
<222> LOCATION: 35
<223> OTHER INFORMATION: /mod_base="m22g"

<400> SEQUENCE: 1
gucaggaugg ccgagugguc uaaggcgcca gacunaaguu cuggucuccg gauggagcgu    60
ggguucgaau cccacuucug acacca                                        86

<210> SEQ ID NO 2
<211> LENGTH: 86
<212> TYPE: RNA
<213> ORGANISM: Artificial Sequence
<220> FEATURE:
<223> OTHER INFORMATION: tRNA Leu with modified anticodon

<400> SEQUENCE: 2
gucaggaugg ccgagugguc uaaggcgcca gacuuaaguu cuggucuccg gauggagcgu    60
ggguucgaau cccacuucug acacca                                        86

<210> SEQ ID NO 3
<211> LENGTH: 89
<212> TYPE: RNA
<213> ORGANISM: Artificial Sequence
<220> FEATURE:
<223> OTHER INFORMATION: tRNA design 1.1 with 10nt anticodon loop =
      tRNA-L3
<220> FEATURE:
<221> NAME/KEY: misc_structure
<222> LOCATION: 32..41
<223> OTHER INFORMATION: /note="extended anticodon loop"
<220> FEATURE:
<221> NAME/KEY: misc_feature
<222> LOCATION: 35..40
<223> OTHER INFORMATION: /note="anticodon tandem"

<400> SEQUENCE: 3
gucaggaugg ccgagugguc uaaggcgcca gacucaguua guucuggucu ccggauggag    60
cguggguucg aaucccacuu cugacacca                                     89

<210> SEQ ID NO 4
<211> LENGTH: 88
<212> TYPE: RNA
<213> ORGANISM: Artificial Sequence
<220> FEATURE:
<223> OTHER INFORMATION: tRNA design 1.2 with 9nt anticodon loop =
      tRNA-L8
<220> FEATURE:
<221> NAME/KEY: misc_structure
<222> LOCATION: 32..40
<223> OTHER INFORMATION: /note="extended anticodon loop"
<220> FEATURE:
<221> NAME/KEY: misc_feature
<222> LOCATION: 34..39
<223> OTHER INFORMATION: /note="anticodon tandem"

<400> SEQUENCE: 4
gucaggaugg ccgagugguc uaaggcgcca gaucaguuag uucuggucuc cggauggagc    60 gugggulrcga aucccacuuc ugacacca                                     88

<210> SEQ ID NO 5
<211> LENGTH: 88
<212> TYPE: RNA
<213> ORGANISM: Artificial Sequence
<220> FEATURE:
<223> OTHER INFORMATION: tRNA design 1.3 with 9nt anticodon loop

<400> SEQUENCE: 5
gucaggaugg ccgagugguc uaaggcgcca gaccaguuag uucuggucuc cggauggagc    60 gugggulrcga aucccacuuc ugacacca                                     88

```
<210> SEQ ID NO 6
<211> LENGTH: 88
<212> TYPE: RNA
<213> ORGANISM: Artificial Sequence
<220> FEATURE:
<223> OTHER INFORMATION: tRNA design 1.4 with 9nt anticodon loop =
      tRNA L9
<220> FEATURE:
<221> NAME/KEY: misc_structure
<222> LOCATION: 32..40
<223> OTHER INFORMATION: /note="extended anticodon loop"
<220> FEATURE:
<221> NAME/KEY: misc_feature
<222> LOCATION: 35..40
<223> OTHER INFORMATION: /note="anticodon tandem"

<400> SEQUENCE: 6
gucaggaugg ccgagugguc uaaggcgcca gacucaguua uucggucuc cggauggagc      60 gugguucga aucccacuuc ugacacca                                        88

<210> SEQ ID NO 7
<211> LENGTH: 88
<212> TYPE: RNA
<213> ORGANISM: Artificial Sequence
<220> FEATURE:
<223> OTHER INFORMATION: tRNA design 1.5 with 9nt anticodon loop

<400> SEQUENCE: 7
gucaggaugg ccgagugguc uaaggcgcca gacucaguua gucggucuc cggauggagc      60 gugguucga aucccacuuc ugacacca                                        88

<210> SEQ ID NO 8
<211> LENGTH: 83
<212> TYPE: RNA
<213> ORGANISM: Thermus thermophilus
<220> FEATURE:
<223> OTHER INFORMATION: tRNA Leu CAG

<400> SEQUENCE: 8
gccggggugg cggaaugggu agacgcgcau gacucaggau caugugcgca agcgugcggg     60
uucaaguccc gccccggca cca                                             83

<210> SEQ ID NO 9
<211> LENGTH: 88
<212> TYPE: RNA
<213> ORGANISM: Artificial Sequence
<220> FEATURE:
<223> OTHER INFORMATION: tRNA design 2.1
<220> FEATURE:
<221> NAME/KEY: misc_feature
<222> LOCATION: 35..40
<223> OTHER INFORMATION: /note="anticodon tandem"

<400> SEQUENCE: 9
ggcaggcuga gggagauggu caaccuagcc agcucaguua gcuggcucuc cggauggagc     60
guggcuucga augccacgcc ugccacca                                       88

<210> SEQ ID NO 10
<211> LENGTH: 88
<212> TYPE: RNA
<213> ORGANISM: Artificial Sequence
<220> FEATURE:
<223> OTHER INFORMATION: tRNA design 2.2
<220> FEATURE:
<221> NAME/KEY: misc_feature
<222> LOCATION: 35..40
```

<223> OTHER INFORMATION: /note="anticodon tandem"

<400> SEQUENCE: 10
gacaggcuga gggagauggu caaccuagca gccucaguua ggcugcucuc cggauggagc   60
guggcuucga augccacgcc ugcacca   88

<210> SEQ ID NO 11
<211> LENGTH: 88
<212> TYPE: RNA
<213> ORGANISM: Artificial Sequence
<220> FEATURE:
<223> OTHER INFORMATION: tRNA design 2.3
<220> FEATURE:
<221> NAME/KEY: misc_feature
<222> LOCATION: 35..40
<223> OTHER INFORMATION: /note="anticodon tandem"

<400> SEQUENCE: 11
gccagccuga gggagauggu caaccuagcc agcucaguua gcuggcucuc cggauggagc   60
guggcuucga augccacggc uggcacca   88

<210> SEQ ID NO 12
<211> LENGTH: 88
<212> TYPE: RNA
<213> ORGANISM: Artificial Sequence
<220> FEATURE:
<223> OTHER INFORMATION: tRNA design 2.4
<220> FEATURE:
<221> NAME/KEY: misc_feature
<222> LOCATION: 35..40
<223> OTHER INFORMATION: /note="anticodon tandem"

<400> SEQUENCE: 12
ggcagccuga gggagauggu caaccuagca gccucaguua ggcugcucuc cggauggagc   60
guggcuucga augccacggc ugccacca   88

<210> SEQ ID NO 13
<211> LENGTH: 88
<212> TYPE: RNA
<213> ORGANISM: Artificial Sequence
<220> FEATURE:
<223> OTHER INFORMATION: tRNA design 2.5
<220> FEATURE:
<221> NAME/KEY: misc_feature
<222> LOCATION: 35..40
<223> OTHER INFORMATION: /note="anticodon tandem"

<400> SEQUENCE: 13
gccagccuga gggagauggu caaccuaggu gccucaguua ggcaccucuc cggauggagc   60
guggcuucga augccacggc uggcacca   88

<210> SEQ ID NO 14
<211> LENGTH: 88
<212> TYPE: RNA
<213> ORGANISM: Artificial Sequence
<220> FEATURE:
<223> OTHER INFORMATION: tRNA design 2.6
<220> FEATURE:
<221> NAME/KEY: misc_feature
<222> LOCATION: 35..40
<223> OTHER INFORMATION: /note="anticodon tandem"

<400> SEQUENCE: 14
gccagccuga gggagauggu caaccuacug gacucaguua guccagucuc cggauggagc   60
guggcuucga augccacggc uggcacca   88

<210> SEQ ID NO 15
<211> LENGTH: 88
<212> TYPE: RNA
<213> ORGANISM: Artificial Sequence
<220> FEATURE:
<223> OTHER INFORMATION: tRNA design 2.7
<220> FEATURE:
<221> NAME/KEY: misc_feature
<222> LOCATION: 35..40
<223> OTHER INFORMATION: /note="anticodon tandem"

<400> SEQUENCE: 15
gccagccuga gggagauggu caaccuaccg gacucaguua guccggucuc cggauggagc    60
guggcuucga augccacggc uggcacca                                       88

<210> SEQ ID NO 16
<211> LENGTH: 88
<212> TYPE: RNA
<213> ORGANISM: Artificial Sequence
<220> FEATURE:
<223> OTHER INFORMATION: tRNA design 2.8
<220> FEATURE:
<221> NAME/KEY: misc_feature
<222> LOCATION: 35..40
<223> OTHER INFORMATION: /note="anticodon tandem"

<400> SEQUENCE: 16
gccagccuga gggagauggu caaccuaccu gccucaguua ggcaggucuc cggauggagc    60
guggcuucga augccacggc uggcacca                                       88

<210> SEQ ID NO 17
<211> LENGTH: 88
<212> TYPE: RNA
<213> ORGANISM: Artificial Sequence
<220> FEATURE:
<223> OTHER INFORMATION: tRNA design 2.9
<220> FEATURE:
<221> NAME/KEY: misc_feature
<222> LOCATION: 35..40
<223> OTHER INFORMATION: /note="anticodon tandem"

<400> SEQUENCE: 17
gccaggcuga gggagauggu caaccuagcu cacucaguua gugagcucuc cggauggagc    60
guggcuucga augccacgcc uggcacca                                       88

<210> SEQ ID NO 18
<211> LENGTH: 72
<212> TYPE: RNA
<213> ORGANISM: Homo sapiens
<220> FEATURE:
<223> OTHER INFORMATION: tRNA Ala-AGC

<400> SEQUENCE: 18
ggggaauuag cucaaauggu agagcgcucg cuuagcaugc gagagguagc gggaucgaug    60
cccgcauucu cc                                                        72

<210> SEQ ID NO 19
<211> LENGTH: 79
<212> TYPE: RNA
<213> ORGANISM: Artificial Sequence
<220> FEATURE:
<223> OTHER INFORMATION: tRNA design 3.1
<220> FEATURE:
<221> NAME/KEY: misc_feature
<222> LOCATION: 34..39

<223> OTHER INFORMATION: /note="anticodon tandem"

<400> SEQUENCE: 19
ggggaauuag cucaaauggu agagcgcucg cuuugcucaa ugcgagaggu agcgggaucg    60
augcccgcau ucuccacca                                                79

<210> SEQ ID NO 20
<211> LENGTH: 78
<212> TYPE: RNA
<213> ORGANISM: Artificial Sequence
<220> FEATURE:
<223> OTHER INFORMATION: tRNA design 3.2
<220> FEATURE:
<221> NAME/KEY: misc_feature
<222> LOCATION: 33..38
<223> OTHER INFORMATION: /note="anticodon tandem"

<400> SEQUENCE: 20
ggggaauuag cucaaauggu agagcgcucg cuugcucaau gcgagaggua gcgggaucga    60
ugcccgcauu cuccacca                                                 78

<210> SEQ ID NO 21
<211> LENGTH: 78
<212> TYPE: RNA
<213> ORGANISM: Artificial Sequence
<220> FEATURE:
<223> OTHER INFORMATION: tRNA design 3.3
<220> FEATURE:
<221> NAME/KEY: misc_feature
<222> LOCATION: 34..39
<223> OTHER INFORMATION: /note="anticodon tandem"

<400> SEQUENCE: 21
ggggaauuag cucaaauggu agagcgcucg cuuugcucau gcgagaggua gcgggaucga    60
ugcccgcauu cuccacca                                                 78

<210> SEQ ID NO 22
<211> LENGTH: 78
<212> TYPE: RNA
<213> ORGANISM: Artificial Sequence
<220> FEATURE:
<223> OTHER INFORMATION: tRNA design 3.4
<220> FEATURE:
<221> NAME/KEY: misc_feature
<222> LOCATION: 34..39
<223> OTHER INFORMATION: /note="anticodon tandem"

<400> SEQUENCE: 22
ggggaauuag cucaaauggu agagcgcucg cuuugcucaa gcgagaggua gcgggaucga    60
ugcccgcauu cuccacca                                                 78

<210> SEQ ID NO 23
<211> LENGTH: 78
<212> TYPE: RNA
<213> ORGANISM: Artificial Sequence
<220> FEATURE:
<223> OTHER INFORMATION: 2x3nt anticodon tRNA based on Ala tRNA
<220> FEATURE:
<221> NAME/KEY: misc_feature
<222> LOCATION: 5..7
<223> OTHER INFORMATION: /note="n = A, C, G or U, or any modified base"
<220> FEATURE:
<221> NAME/KEY: misc_feature
<222> LOCATION: 16..17
<223> OTHER INFORMATION: /note="n = A, C, G, or U, or any modified base"
<220> FEATURE:
<221> NAME/KEY: misc_feature -continued

```
<222> LOCATION: 27..31
<223> OTHER INFORMATION: /note="n = A, C, G, or U, or any modified base"
<220> FEATURE:
<221> NAME/KEY: misc_feature
<222> LOCATION: 34..39
<223> OTHER INFORMATION: /note="anticodon tandem"
<220> FEATURE:
<221> NAME/KEY: misc_feature
<222> LOCATION: 41..45
<223> OTHER INFORMATION: /note="n = A, C, G, or U, or any modified base"
<220> FEATURE:
<221> NAME/KEY: misc_feature
<222> LOCATION: 47
<223> OTHER INFORMATION: /note="n = A, C, G, or U, or any modified base"
<220> FEATURE:
<221> NAME/KEY: misc_feature
<222> LOCATION: 49
<223> OTHER INFORMATION: /note="n = A, C, G, or U, or any modified base"
<220> FEATURE:
<221> NAME/KEY: misc_feature
<222> LOCATION: 51..54
<223> OTHER INFORMATION: /note="n = A, C, G, or U, or any modified base"
<220> FEATURE:
<221> NAME/KEY: misc_feature
<222> LOCATION: 64..70
<223> OTHER INFORMATION: /note="n = A, C, G, or U, or any modified base"

<400> SEQUENCE: 23
ggggnnnuag cucagnnggu agagcgnnnn ncuugcucaa nnnnnangnc nnnnguucga    60
uccnnnnnnn cuccacca                                                 78

<210> SEQ ID NO 24
<211> LENGTH: 74
<212> TYPE: RNA
<213> ORGANISM: Artificial Sequence
<220> FEATURE:
<223> OTHER INFORMATION: 2x3nt anticodon tRNA based on Ala tRNA without
      CCA tail
<220> FEATURE:
<221> NAME/KEY: misc_feature
<222> LOCATION: 5..7
<223> OTHER INFORMATION: /note="n = A, C, G or U, or any modified base"
<220> FEATURE:
<221> NAME/KEY: misc_feature
<222> LOCATION: 16..17
<223> OTHER INFORMATION: /note="n = A, C, G, or U, or any modified base"
<220> FEATURE:
<221> NAME/KEY: misc_feature
<222> LOCATION: 27..31
<223> OTHER INFORMATION: /note="n = A, C, G, or U, or any modified base"
<220> FEATURE:
<221> NAME/KEY: misc_feature
<222> LOCATION: 34..39
<223> OTHER INFORMATION: /note="anticodon tandem"
<220> FEATURE:
<221> NAME/KEY: misc_feature
<222> LOCATION: 41..45
<223> OTHER INFORMATION: /note="n = A, C, G, or U, or any modified base"
<220> FEATURE:
<221> NAME/KEY: misc_feature
<222> LOCATION: 47
<223> OTHER INFORMATION: /note="n = A, C, G, or U, or any modified base"
<220> FEATURE:
<221> NAME/KEY: misc_feature
<222> LOCATION: 49
<223> OTHER INFORMATION: /note="n = A, C, G, or U, or any modified base"
<220> FEATURE:
<221> NAME/KEY: misc_feature
<222> LOCATION: 51..54
<223> OTHER INFORMATION: /note="n = A, C, G, or U, or any modified base"
<220> FEATURE:
<221> NAME/KEY: misc_feature
<222> LOCATION: 64..70
<223> OTHER INFORMATION: /note="n = A, C, G, or U, or any modified base"

<400> SEQUENCE: 24
```
ggggnnnuag cucagnnggu agagcgnnnn ncuugcucaa nnnnnangnc nnnnguucga    60
uccnnnnnnn cucc    74

<210> SEQ ID NO 25
<211> LENGTH: 78
<212> TYPE: RNA
<213> ORGANISM: Artificial Sequence
<220> FEATURE:
<223> OTHER INFORMATION: tRNA with extended anticodon loop
<220> FEATURE:
<221> NAME/KEY: misc_feature
<222> LOCATION: 32..40
<223> OTHER INFORMATION: /note="n = A, C, G or U, or any modified base"
<220> FEATURE:
<221> NAME/KEY: misc_structure
<222> LOCATION: 32..40
<223> OTHER INFORMATION: /note="extended anticodon loop"

<400> SEQUENCE: 25
ggggcgguag cucagaaggg agagcagcgg annnnnnnnn uccgcgagac gguccuucga    60
uuggaccccg cuccacca    78

<210> SEQ ID NO 26
<211> LENGTH: 76
<212> TYPE: RNA
<213> ORGANISM: Artificial Sequence
<220> FEATURE:
<223> OTHER INFORMATION: tRNA with extended anticodon loop
<220> FEATURE:
<221> NAME/KEY: misc_feature
<222> LOCATION: 31..39
<223> OTHER INFORMATION: /note="extended anticodon loop"
<220> FEATURE:
<221> NAME/KEY: misc_feature
<222> LOCATION: 31..39
<223> OTHER INFORMATION: /note="n = A, C, G or U, or any modified base"

<400> SEQUENCE: 26
ggggcgguag cucagaaggg agagcagcgg nnnnnnnnnc cgcgagacag ggguucgauu    60
ccccuccgcu ccacca    76

<210> SEQ ID NO 27
<211> LENGTH: 77
<212> TYPE: RNA
<213> ORGANISM: Artificial Sequence
<220> FEATURE:
<223> OTHER INFORMATION: tRNA with extended anticodon loop
<220> FEATURE:
<221> NAME/KEY: misc_feature
<222> LOCATION: 10..26
<223> OTHER INFORMATION: /note="D arm"
<220> FEATURE:
<221> NAME/KEY: misc_feature
<222> LOCATION: 32..40
<223> OTHER INFORMATION: /note="n = A, C, G or U, or any modified base"
<220> FEATURE:
<221> NAME/KEY: misc_structure
<222> LOCATION: 32..40
<223> OTHER INFORMATION: /note="extended anticodon loop"

<400> SEQUENCE: 27
ggggcgguag cgcagccugg uagcgcagcg gnnnnnnnnn ccgcgagaca ggguucgau    60 uccccuccgc uccacca    77

<210> SEQ ID NO 28
<211> LENGTH: 78
<212> TYPE: RNA

```
<213> ORGANISM: Artificial Sequence
<220> FEATURE:
<223> OTHER INFORMATION: tRNA with extended anticodon loop
<220> FEATURE:
<221> NAME/KEY: misc_structure
<222> LOCATION: 32..40
<223> OTHER INFORMATION: /note="extended anticodon loop"

<400> SEQUENCE: 28
ggggcgguag cucagaaggg agagcagcgg acuugcucaa uccgcgagac gguccuucga      60
uuggaccccg cuccacca                                                   78

<210> SEQ ID NO 29
<211> LENGTH: 76
<212> TYPE: RNA
<213> ORGANISM: Artificial Sequence
<220> FEATURE:
<223> OTHER INFORMATION: tRNA with extended anticodon loop
<220> FEATURE:
<221> NAME/KEY: misc_structure
<222> LOCATION: 31..39
<223> OTHER INFORMATION: /note="extended anticodon loop"

<400> SEQUENCE: 29
ggggcgguag cucagaaggg agagcagcgg cuugcucaac cgcgagacag ggguucgauu      60
ccccuccgcu ccacca                                                     76

<210> SEQ ID NO 30
<211> LENGTH: 77
<212> TYPE: RNA
<213> ORGANISM: Artificial Sequence
<220> FEATURE:
<223> OTHER INFORMATION: tRNA with extended anticodon loop
<220> FEATURE:
<221> NAME/KEY: misc_feature
<222> LOCATION: 10..26
<223> OTHER INFORMATION: /note="D arm"
<220> FEATURE:
<221> NAME/KEY: misc_structure
<222> LOCATION: 32..40
<223> OTHER INFORMATION: /note="extended anticodon loop"

<400> SEQUENCE: 30
ggggcgguag cgcagccugg uagcgcagcg gcuugcucaa ccgcgagaca ggguucgau      60 uccccuccgc uccacca                                                    77

<210> SEQ ID NO 31
<211> LENGTH: 17
<212> TYPE: RNA
<213> ORGANISM: Artificial Sequence
<220> FEATURE:
<223> OTHER INFORMATION: modified D-arm

<400> SEQUENCE: 31
gcgcagccug guagcgc                                                    17

<210> SEQ ID NO 32
<211> LENGTH: 17
<212> TYPE: DNA
<213> ORGANISM: T7-like viruses
<220> FEATURE:
<223> OTHER INFORMATION: T7 promoter

<400> SEQUENCE: 32
taatacgact cactata                                                    17
```

-continued

```
<210> SEQ ID NO 33
<211> LENGTH: 76
<212> TYPE: RNA
<213> ORGANISM: Artificial Sequence
<220> FEATURE:
<223> OTHER INFORMATION: n1 tRNA with antistop codon
<220> FEATURE:
<221> NAME/KEY: misc_structure
<222> LOCATION: 34..36
<223> OTHER INFORMATION: /note="antistop codon"

<400> SEQUENCE: 33
ggggcgguag cucagaaggg agagcagcgg agaucaaauc cgcgagacgg uccuucgauu     60
ggaccccgcu ccacca                                                    76

<210> SEQ ID NO 34
<211> LENGTH: 76
<212> TYPE: RNA
<213> ORGANISM: Artificial Sequence
<220> FEATURE:
<223> OTHER INFORMATION: n2 tRNA with antistop codon
<220> FEATURE:
<221> NAME/KEY: misc_structure
<222> LOCATION: 34..36
<223> OTHER INFORMATION: /note="antistop codon"

<400> SEQUENCE: 34
ggggcucuag cucagaaggg agagcaggga cgaucaaagu cccgagacgg cgcuucgauu     60
gcgccgagcu ccacca                                                    76

<210> SEQ ID NO 35
<211> LENGTH: 76
<212> TYPE: RNA
<213> ORGANISM: Artificial Sequence
<220> FEATURE:
<223> OTHER INFORMATION: n3 tRNA with antistop codon
<220> FEATURE:
<221> NAME/KEY: misc_structure
<222> LOCATION: 34..36
<223> OTHER INFORMATION: /note="antistop codon"

<400> SEQUENCE: 35
ggggcccuag cucagaaagg agagcaggca ggaucaaacu gccgagaagc agcgacauaa     60
gcugcgggcu ccacca                                                    76

<210> SEQ ID NO 36
<211> LENGTH: 76
<212> TYPE: RNA
<213> ORGANISM: Artificial Sequence
<220> FEATURE:
<223> OTHER INFORMATION: n4 tRNA with antistop codon
<220> FEATURE:
<221> NAME/KEY: misc_structure
<222> LOCATION: 34..36
<223> OTHER INFORMATION: /note="antistop codon"

<400> SEQUENCE: 36
ggggcccuag cucagaaagg agagcaggca ggacuaaacu gccgagaagc cgggacuaaa     60
ccggcgggcu ccacca                                                    76

<210> SEQ ID NO 37
<211> LENGTH: 76
<212> TYPE: RNA
<213> ORGANISM: Artificial Sequence
<220> FEATURE:
<223> OTHER INFORMATION: n5 tRNA with antistop codon
<220> FEATURE:
```

```
<221> NAME/KEY: misc_structure
<222> LOCATION: 34..36
<223> OTHER INFORMATION: /note="antistop codon"

<400> SEQUENCE: 37
ggggcgcuag cucaauaagg agagcaggag cgacuaaagc uccgagaagu cgcgacauaa    60
gcgacgcgcu ccacca                                                   76

<210> SEQ ID NO 38
<211> LENGTH: 76
<212> TYPE: RNA
<213> ORGANISM: Artificial Sequence
<220> FEATURE:
<223> OTHER INFORMATION: n6 tRNA with antistop codon
<220> FEATURE:
<221> NAME/KEY: misc_structure
<222> LOCATION: 34..36
<223> OTHER INFORMATION: /note="antistop codon"

<400> SEQUENCE: 38
ggggcggaac agggaaacag accugagcgg agacuaaauc cgcaauaagg uccgaacuaa    60
ggaccccgcu ccacca                                                   76

<210> SEQ ID NO 39
<211> LENGTH: 76
<212> TYPE: RNA
<213> ORGANISM: Homo sapiens
<220> FEATURE:
<223> OTHER INFORMATION: Human Ala tRNA (GGC)
<220> FEATURE:
<221> NAME/KEY: misc_structure
<222> LOCATION: 34..36
<223> OTHER INFORMATION: /note="anticodon"

<400> SEQUENCE: 39
ggggcuauag cucagcuggg agagcgcuug cauggcaugc aagaggucag cgguucgauc    60
ccgcuuagcu ccacca                                                   76

<210> SEQ ID NO 40
<211> LENGTH: 76
<212> TYPE: RNA
<213> ORGANISM: Homo sapiens
<220> FEATURE:
<223> OTHER INFORMATION: Human Ala tRNA (UGC)
<220> FEATURE:
<221> NAME/KEY: misc_structure
<222> LOCATION: 34..36
<223> OTHER INFORMATION: /note="anticodon"

<400> SEQUENCE: 40
ggggcuauag cucagcuggg agagcgccug cuuugcacgc aggaggucug cgguucgauc    60
ccgcauagcu ccacca                                                   76

<210> SEQ ID NO 41
<211> LENGTH: 76
<212> TYPE: RNA
<213> ORGANISM: Artificial Sequence
<220> FEATURE:
<223> OTHER INFORMATION: Human tRNA Ala with antistop codon
<220> FEATURE:
<221> NAME/KEY: misc_structure
<222> LOCATION: 34..36
<223> OTHER INFORMATION: /note="antistop codon"

<400> SEQUENCE: 41
ggggcuauag cucagcuggg agagcgccug cuuucaacgc aggaggucug cgguucgauc    60
```

```
ccgcauagcu ccacca                                              76
```

```
<210> SEQ ID NO 42
<211> LENGTH: 76
<212> TYPE: RNA
<213> ORGANISM: Artificial Sequence
<220> FEATURE:
<223> OTHER INFORMATION: TS1: tRNA with antistop codon and modified
      T-stem
<220> FEATURE:
<221> NAME/KEY: misc_structure
<222> LOCATION: 34..36
<223> OTHER INFORMATION: /note="antistop codon"
<220> FEATURE:
<221> NAME/KEY: misc_structure
<222> LOCATION: 49..53
<223> OTHER INFORMATION: /note="T-stem"
<220> FEATURE:
<221> NAME/KEY: misc_structure
<222> LOCATION: 61..65
<223> OTHER INFORMATION: /note="T-stem"

<400> SEQUENCE: 42
ggggcgguag cucagaaggg agagcagcgg ccuucagagc cgcgagacug cccuucgauu    60
gggcaccgcu ccacca                                                   76
```

```
<210> SEQ ID NO 43
<211> LENGTH: 76
<212> TYPE: RNA
<213> ORGANISM: Artificial Sequence
<220> FEATURE:
<223> OTHER INFORMATION: TS2: tRNA with antistop codon and modified
      T-stem
<220> FEATURE:
<221> NAME/KEY: misc_structure
<222> LOCATION: 34..36
<223> OTHER INFORMATION: /note="antistop codon"
<220> FEATURE:
<221> NAME/KEY: misc_structure
<222> LOCATION: 49..53
<223> OTHER INFORMATION: /note="T-stem"
<220> FEATURE:
<221> NAME/KEY: misc_structure
<222> LOCATION: 61..65
<223> OTHER INFORMATION: /note="T-stem"

<400> SEQUENCE: 43
ggggcgguag cucagaaggg agagcagcgg ccuucagagc cgcgagacag ggguucgauu    60
ccccuccgcu ccacca                                                   76
```

```
<210> SEQ ID NO 44
<211> LENGTH: 77
<212> TYPE: RNA
<213> ORGANISM: Artificial Sequence
<220> FEATURE:
<223> OTHER INFORMATION: DTS1: tRNA with antistop codon, modified T-stem
      and modified D-Loop
<220> FEATURE:
<221> NAME/KEY: misc_structure
<222> LOCATION: 10..26
<223> OTHER INFORMATION: /note="D arm"
<220> FEATURE:
<221> NAME/KEY: misc_structure
<222> LOCATION: 35..37
<223> OTHER INFORMATION: /note="antistop codon"
<220> FEATURE:
<221> NAME/KEY: misc_structure
<222> LOCATION: 50..54
<223> OTHER INFORMATION: /note="T-stem"
<220> FEATURE:
<221> NAME/KEY: misc_structure
```

<222> LOCATION: 62..66
<223> OTHER INFORMATION: /note="T-stem"

<400> SEQUENCE: 44
ggggcgguag cgcagccugg uagcgcagcg gccuucagag ccgcgagacu gcccuucgau    60
ugggcaccgc uccacca                                                   77

<210> SEQ ID NO 45
<211> LENGTH: 77
<212> TYPE: RNA
<213> ORGANISM: Artificial Sequence
<220> FEATURE:
<223> OTHER INFORMATION: DTS2: tRNA with antistop codon, modified T-stem
      and modified D-Loop
<220> FEATURE:
<221> NAME/KEY: misc_binding
<222> LOCATION: 10..26
<223> OTHER INFORMATION: /note="D arm"
<220> FEATURE:
<221> NAME/KEY: misc_structure
<222> LOCATION: 35..37
<223> OTHER INFORMATION: /note="antistop codon"
<220> FEATURE:
<221> NAME/KEY: misc_structure
<222> LOCATION: 50..54
<223> OTHER INFORMATION: /note="T-stem"
<220> FEATURE:
<221> NAME/KEY: misc_structure
<222> LOCATION: 62..66
<223> OTHER INFORMATION: /note="T-stem"

<400> SEQUENCE: 45
ggggcgguag cgcagccugg uagcgcagcg gccuucagag ccgcgagaca gggguucgau    60
uccccuccgc uccacca                                                   77

<210> SEQ ID NO 46
<211> LENGTH: 89
<212> TYPE: RNA
<213> ORGANISM: Artificial Sequence
<220> FEATURE:
<223> OTHER INFORMATION: tRNA-L1 with extended anticodon loop
<220> FEATURE:
<221> NAME/KEY: misc_structure
<222> LOCATION: 32..41
<223> OTHER INFORMATION: /note="extended anticodon loop"
<220> FEATURE:
<221> NAME/KEY: misc_feature
<222> LOCATION: 34..39
<223> OTHER INFORMATION: /note="anticodon tandem"

<400> SEQUENCE: 46
gucaggaugg ccgagugguc uaaggcgcca ccucaguuag agucuggucu ccggauggag    60
cguggguucg aauccacuu cugacacca                                       89

<210> SEQ ID NO 47
<211> LENGTH: 89
<212> TYPE: RNA
<213> ORGANISM: Artificial Sequence
<220> FEATURE:
<223> OTHER INFORMATION: tRNA-L2 with extended anticodon loop
<220> FEATURE:
<221> NAME/KEY: misc_structure
<222> LOCATION: 32..41
<223> OTHER INFORMATION: /note="extended anticodon loop"
<220> FEATURE:
<221> NAME/KEY: misc_feature
<222> LOCATION: 34..39
<223> OTHER INFORMATION: /note="anticodon tandem"

<400> SEQUENCE: 47
gucaggaugg ccgagugguc uaaggcgcca ccucaguuaa agucuggucu ccggauggag    60 cgugggttucg aaucccacuu cugacacca                                    89

<210> SEQ ID NO 48
<211> LENGTH: 88
<212> TYPE: RNA
<213> ORGANISM: Artificial Sequence
<220> FEATURE:
<223> OTHER INFORMATION: tRNA-L4 with extended anticodon loop
<220> FEATURE:
<221> NAME/KEY: misc_structure
<222> LOCATION: 32..40
<223> OTHER INFORMATION: /note="extended anticodon loop"
<220> FEATURE:
<221> NAME/KEY: misc_feature
<222> LOCATION: 34..39
<223> OTHER INFORMATION: /note="anticodon tandem"

<400> SEQUENCE: 48
gucaggaugg ccgaguggtuc uaaggcgcca ccucaguuag gucuggucuc cggauggagc    60 gugggutucga aucccacuuc ugacacca                                     88

<210> SEQ ID NO 49
<211> LENGTH: 88
<212> TYPE: RNA
<213> ORGANISM: Artificial Sequence
<220> FEATURE:
<223> OTHER INFORMATION: tRNA-L5 with extended anticodon loop
<220> FEATURE:
<221> NAME/KEY: misc_structure
<222> LOCATION: 32..40
<223> OTHER INFORMATION: /note="extended anticodon loop"
<220> FEATURE:
<221> NAME/KEY: misc_feature
<222> LOCATION: 34..39
<223> OTHER INFORMATION: /note="anticodon tandem"

<400> SEQUENCE: 49
gucaggaugg ccgaguggtuc uaaggcgcca ccucaguuaa gucuggucuc cggauggagc    60 gugggutucga aucccacuuc ugacacca                                     88

<210> SEQ ID NO 50
<211> LENGTH: 88
<212> TYPE: RNA
<213> ORGANISM: Artificial Sequence
<220> FEATURE:
<223> OTHER INFORMATION: tRNA-L6 with extended anticodon loop
<220> FEATURE:
<221> NAME/KEY: misc_structure
<222> LOCATION: 32..40
<223> OTHER INFORMATION: /note="extended anticodon loop"
<220> FEATURE:
<221> NAME/KEY: misc_feature
<222> LOCATION: 34..39
<223> OTHER INFORMATION: /note="anticodon tandem"

<400> SEQUENCE: 50
gucaggaugg ccgaguggtuc uaaggcgcca ccucaguuau gucuggucuc cggauggagc    60 gugggutucga aucccacuuc ugacacca                                     88

<210> SEQ ID NO 51
<211> LENGTH: 10
<212> TYPE: RNA
<213> ORGANISM: Artificial Sequence
<220> FEATURE:
<223> OTHER INFORMATION: tR-L1 anticodon loop

```
<400> SEQUENCE: 51
cucaguuaga                                                              10

<210> SEQ ID NO 52
<211> LENGTH: 10
<212> TYPE: RNA
<213> ORGANISM: Artificial Sequence
<220> FEATURE:
<223> OTHER INFORMATION: tR-L2 anticodon loop

<400> SEQUENCE: 52
cucaguuaaa                                                              10

<210> SEQ ID NO 53
<211> LENGTH: 10
<212> TYPE: RNA
<213> ORGANISM: Artificial Sequence
<220> FEATURE:
<223> OTHER INFORMATION: tR-L3 anticodon loop

<400> SEQUENCE: 53
acucaguuag                                                              10

<210> SEQ ID NO 54
<211> LENGTH: 20
<212> TYPE: RNA
<213> ORGANISM: Artificial Sequence
<220> FEATURE:
<223> OTHER INFORMATION: V loop tRNA selenocysteine

<400> SEQUENCE: 54
uuggggccgc gcggucccgg                                                   20

<210> SEQ ID NO 55
<211> LENGTH: 79
<212> TYPE: RNA
<213> ORGANISM: Artificial Sequence
<220> FEATURE:
<223> OTHER INFORMATION: tRNA with extended anticodon loop
<220> FEATURE:
<221> NAME/KEY: misc_feature
<222> LOCATION: 32..41
<223> OTHER INFORMATION: /note="n = A, C, G or U, or any modified base"
<220> FEATURE:
<221> NAME/KEY: misc_structure
<222> LOCATION: 32..41
<223> OTHER INFORMATION: /note="extended anticodon loop"

<400> SEQUENCE: 55
ggggcgguag cucagaaggg agagcagcgg annnnnnnnn nuccgcgaga cgguccuucg        60
auuggacccc gcuccacca                                                    79

<210> SEQ ID NO 56
<211> LENGTH: 77
<212> TYPE: RNA
<213> ORGANISM: Artificial Sequence
<220> FEATURE:
<223> OTHER INFORMATION: tRNA with extended anticodon loop
<220> FEATURE:
<221> NAME/KEY: misc_feature
<222> LOCATION: 31..40
<223> OTHER INFORMATION: /note="n = A, C, G or U, or any modified base"
<220> FEATURE:
<221> NAME/KEY: misc_structure
<222> LOCATION: 31..40
<223> OTHER INFORMATION: /note="extended anticodon loop"
<220> FEATURE:
<221> NAME/KEY: misc_feature
```

```
<222> LOCATION: 50..54
<223> OTHER INFORMATION: /note="T stem"
<220> FEATURE:
<221> NAME/KEY: misc_feature
<222> LOCATION: 62..66
<223> OTHER INFORMATION: /note="T stem"

<400> SEQUENCE: 56
ggggcgguag cucagaaggg agagcagcgg nnnnnnnnnn ccgcgagaca gggguucgau      60
uccccuccgc uccacca                                                    77

<210> SEQ ID NO 57
<211> LENGTH: 78
<212> TYPE: RNA
<213> ORGANISM: Artificial Sequence
<220> FEATURE:
<223> OTHER INFORMATION: tRNA with extended anticodon loop
<220> FEATURE:
<221> NAME/KEY: misc_feature
<222> LOCATION: 10..26
<223> OTHER INFORMATION: /note="D arm"
<220> FEATURE:
<221> NAME/KEY: misc_feature
<222> LOCATION: 32..41
<223> OTHER INFORMATION: /note="n = A, C, G or U, or any modified base"
<220> FEATURE:
<221> NAME/KEY: misc_structure
<222> LOCATION: 32..41
<223> OTHER INFORMATION: /note="extended anticodon loop"
<220> FEATURE:
<221> NAME/KEY: misc_feature
<222> LOCATION: 51..55
<223> OTHER INFORMATION: /note="T stem"
<220> FEATURE:
<221> NAME/KEY: misc_feature
<222> LOCATION: 63..67
<223> OTHER INFORMATION: /note="T stem"

<400> SEQUENCE: 57
ggggcgguag cgcagccugg uagcgcagcg gnnnnnnnnn nccgcgagac agggguucga      60
uuccccuccg cuccacca                                                   78
```